United States Patent
Tajima

(10) Patent No.: US 9,782,137 B2
(45) Date of Patent: Oct. 10, 2017

(54) RADIOGRAPHIC IMAGING SYSTEM, METHOD OF CONTROLLING RADIOGRAPHIC IMAGING SYSTEM AND RECORDING MEDIUM STORING PROGRAM OF CONTROLLING RADIOGRAPHIC IMAGING SYSTEM

(71) Applicant: FUJIFILM CORPORATION, Minato-ku, Tokyo (JP)

(72) Inventor: Takashi Tajima, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 313 days.

(21) Appl. No.: 14/626,929

(22) Filed: Feb. 20, 2015

(65) Prior Publication Data

US 2015/0257245 A1    Sep. 10, 2015

(30) Foreign Application Priority Data

Mar. 7, 2014    (JP) ................. 2014-045742

(51) Int. Cl.
| | | |
|---|---|---|
| H05G 1/64 | (2006.01) | |
| A61B 6/00 | (2006.01) | |
| G01N 23/04 | (2006.01) | |

(52) U.S. Cl.
CPC ............ A61B 6/4233 (2013.01); A61B 6/542 (2013.01); A61B 6/405 (2013.01); G01N 23/04 (2013.01)

(58) Field of Classification Search
CPC .......... H05G 1/44; G01N 23/04; A61B 6/542; A61B 6/4233; A61B 6/405
USPC .......... 378/62, 114–117; 250/370.08, 370.09
See application file for complete search history.

(56) References Cited

U.S. PATENT DOCUMENTS

2010/0020929 A1*  1/2010  Akahori ............... A61B 6/4233
                                                                378/62

FOREIGN PATENT DOCUMENTS

JP    2002-263089 A    9/2002

OTHER PUBLICATIONS

"AGC Develops World's Thinnest Sheet Float Glass at Just 0.1 MM", AGC Press Release, Tokyo, May 16, 2011 (www.agc.com/english/news/2011/0516e.pdf).

* cited by examiner

Primary Examiner — Courtney Thomas
(74) Attorney, Agent, or Firm — SOLARIS Intellectual Property Group, PLLC

(57) ABSTRACT

A radiographic imaging system that includes: a radiation detector including an imaging region in which a plurality of pixels are provided, each pixel including a sensor portion that generates charges in accordance with radiation amounts of irradiated radiation and accumulates the generated charges during an accumulation period, and a switching element that reads out the charges from the sensor portion after the accumulation period; an imaging control section that images a radiographic image by sequentially imaging radiographic images during the accumulation period using division regions, into which the imaging region of the radiation detector is plurally divided, one at a time; and a display control section that displays, at a display section, information relating to remaining imaging until the imaging is complete, the information representing a state of progress of the imaging by the imaging control section.

9 Claims, 12 Drawing Sheets

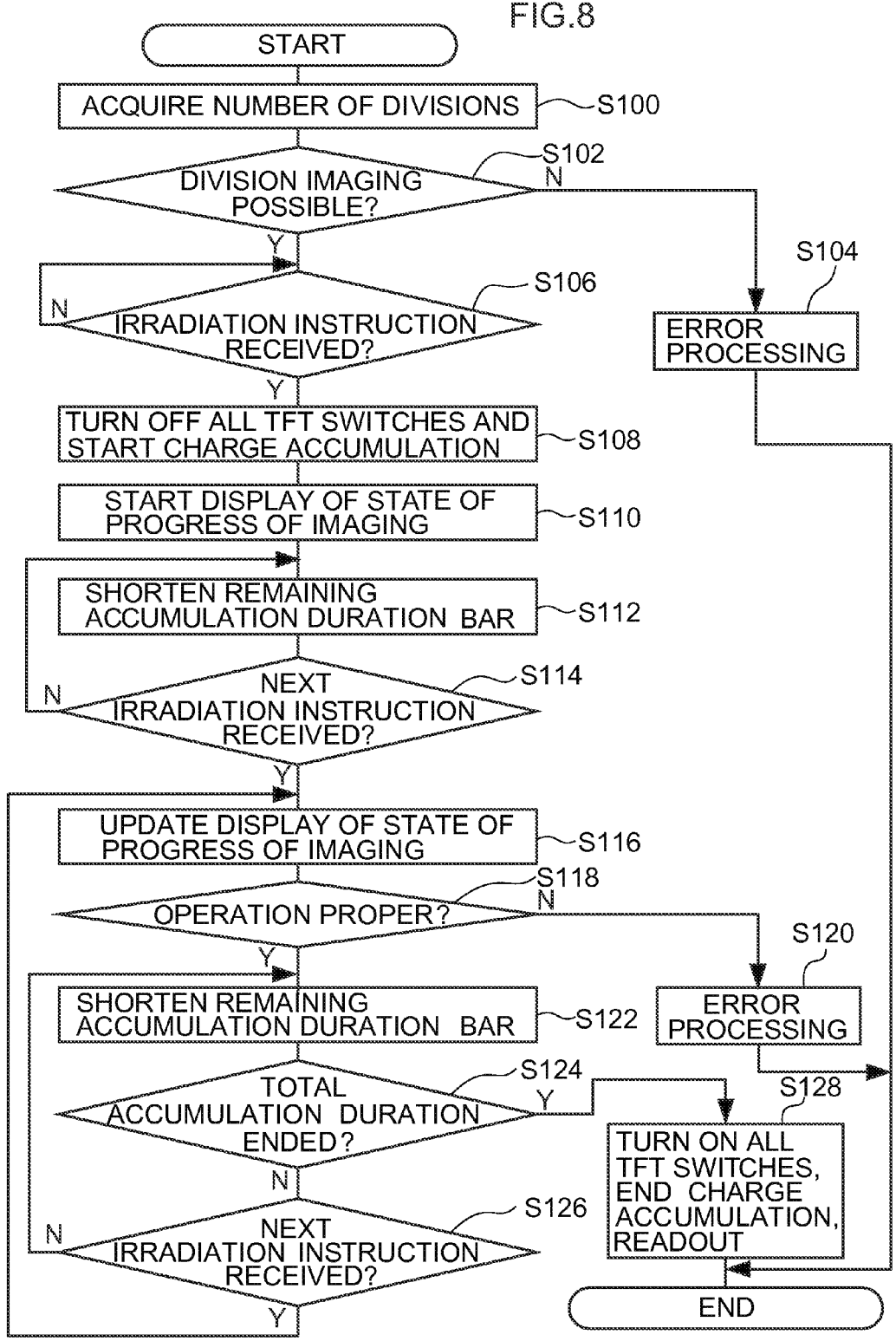

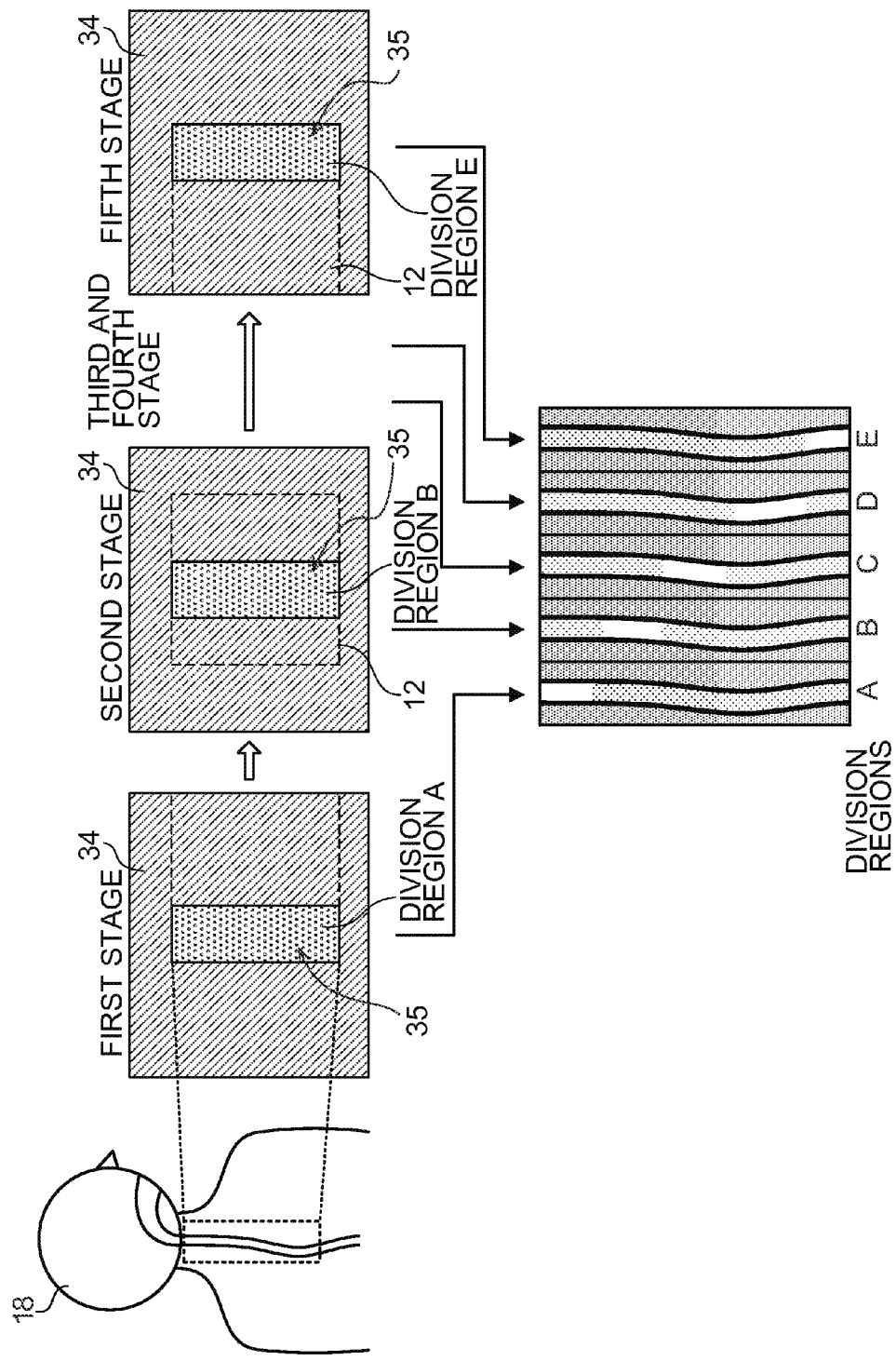

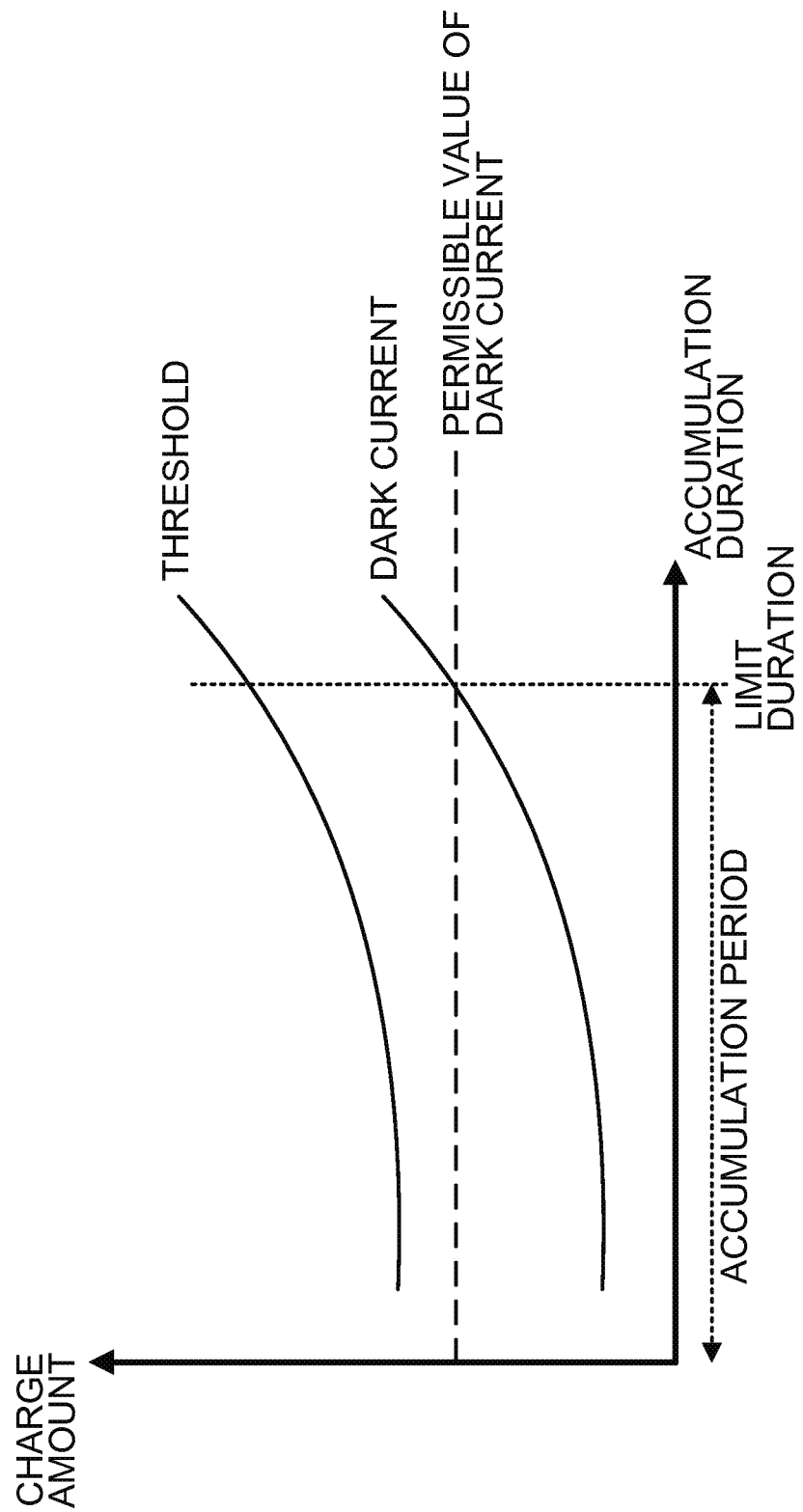

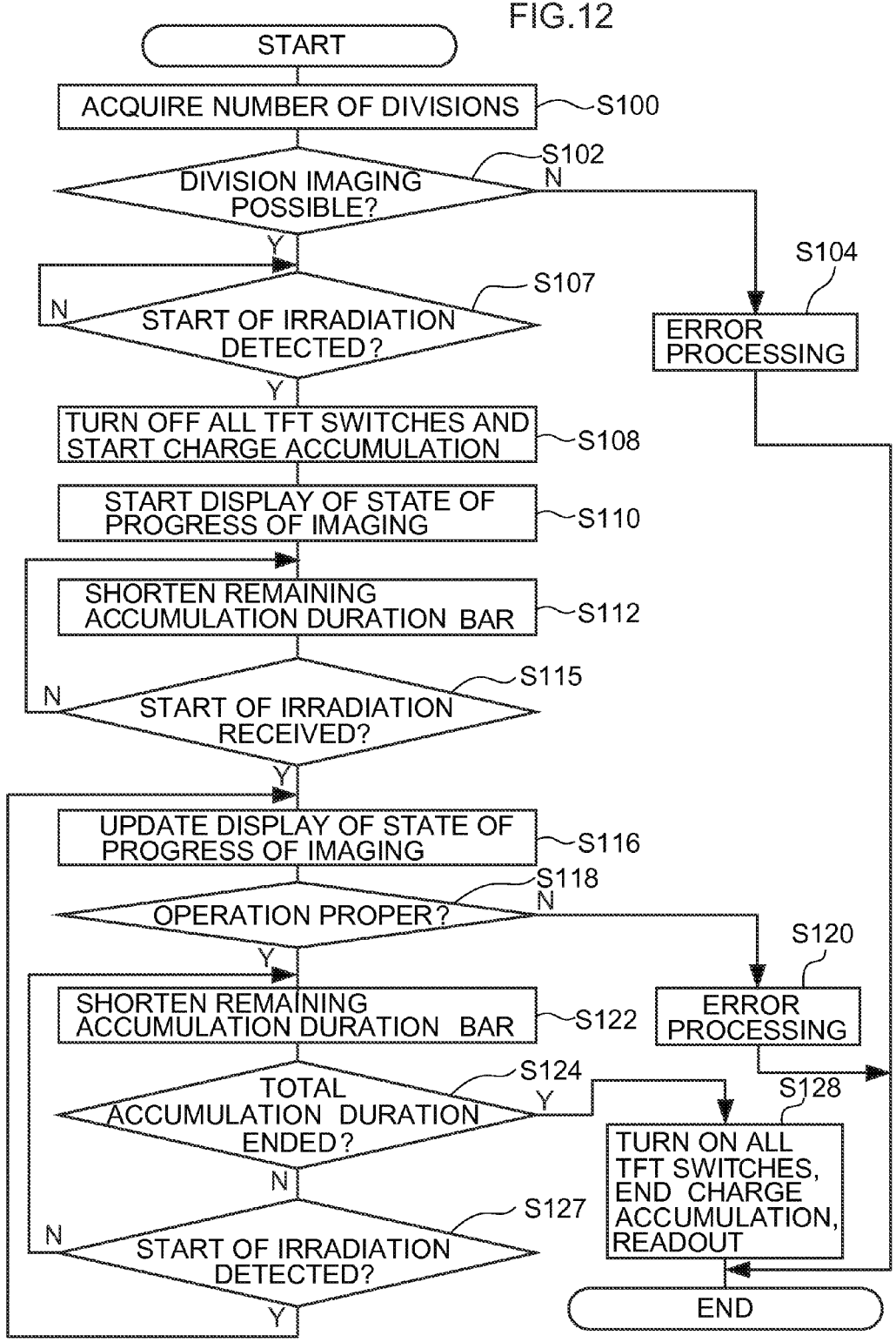

RADIOGRAPHIC IMAGING SYSTEM, METHOD OF CONTROLLING RADIOGRAPHIC IMAGING SYSTEM AND RECORDING MEDIUM STORING PROGRAM OF CONTROLLING RADIOGRAPHIC IMAGING SYSTEM

CROSS-REFERENCE TO RELATED APPLICATION

This application is based upon and claims the benefit of priority of the prior Japanese Patent Application No. 2014-045742, filed on Mar. 7, 2014, the entire contents of which are incorporated herein by reference.

FIELD

The present disclosure relates to a radiographic imaging system, a method of controlling the radiographic imaging system, and a recording medium storing a program for controlling the radiographic imaging system.

BACKGROUND

Radiographic imaging systems that image subjects include a radiographic imaging system that is known to perform radiographic imaging for purposes of, for example, medical diagnostics. This radiographic imaging system detects radiation that has been irradiated from a radiation irradiation device and passed through an imaging subject with a radiation detector to capture a radiographic image. The radiographic imaging system captures the radiographic image by collecting and reading electric charges, which are generated in accordance with the irradiated radiation, from the radiation detector.

Imaging of radiographic images includes division imaging, in which an imaging region of the radiation detector is divided into a plural number of regions and imaging of a radiographic image is carried out at each division region, using one division region at a time (for example, see Japanese Patent Application Laid-Open (JP-A) No. 2002-263089).

Alternatively, there is multiple exposure imaging, in which a multiple exposure is performed by radiation being irradiated at the same imaging region of the radiation detector plural times, to obtain a single radiographic image. This imaging method is used in cases in which sufficient radiation amounts cannot be obtained from a single irradiation; for example, imaging of an imaging subject (patient) whose body has a large thickness with a radiation irradiation device whose output power is low.

SUMMARY

A radiographic imaging system includes: a radiation detector including an imaging region in which a plurality of pixels are provided, each pixel including a sensor portion that generates charges in accordance with radiation amounts of irradiated radiation and accumulates the generated charges during an accumulation period, and a switching element that reads out the charges from the sensor portion after the accumulation period; an imaging control section that images a radiographic image by one of sequentially imaging radiographic images during the accumulation period using division regions, into which the imaging region of the radiation detector is plurally divided, one at a time, or performing a multiple exposure in which the same region of the imaging region of the radiation detector is irradiated plural times during the accumulation period; and a display control section that displays, at a display section, information relating to remaining imaging until the imaging is complete, the information representing a state of progress of the imaging by the imaging control section.

BRIEF DESCRIPTION OF DRAWINGS

FIG. 8 is a flowchart showing an example of the flow of division imaging processing in accordance with the first exemplary embodiment;

FIG. 9 is a descriptive diagram for describing division imaging by the radiographic imaging system in accordance with the first exemplary embodiment;

FIG. 11 is a descriptive diagram for describing an increase in charge amount with accumulation duration due to a dark current; and FIG. 12 is a flowchart showing an example of the flow of division imaging processing in accordance with a second exemplary embodiment.

DESCRIPTION OF EMBODIMENTS

First Exemplary Embodiment

Herebelow, an example of a present exemplary embodiment is described with reference to the attached drawings.

Figure 1:
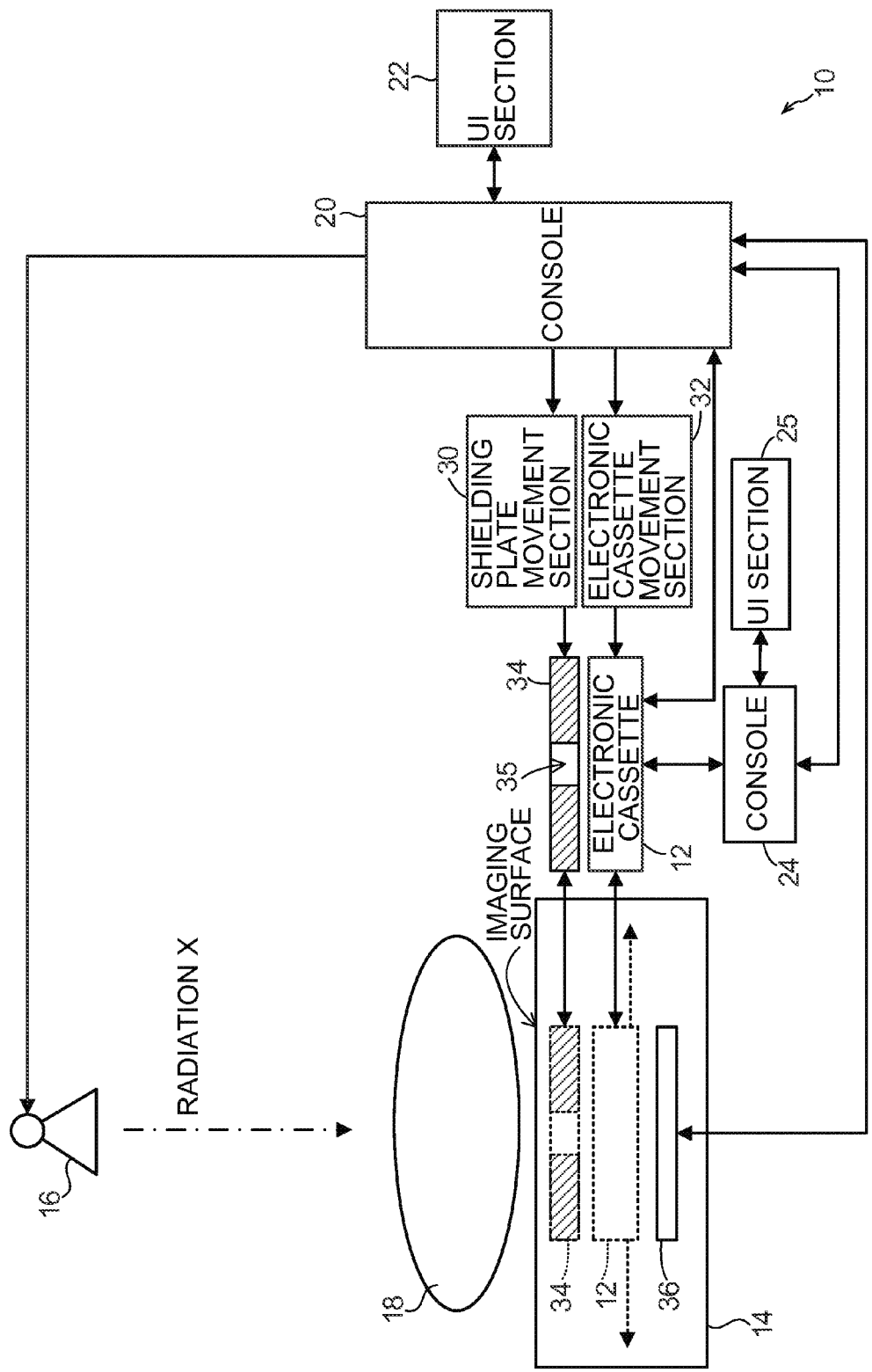
FIG. 1 is a schematic structural diagram showing general structure of an example of a radiographic imaging system in accordance with a first exemplary embodiment.

First, the overall schematic structure of a radiographic imaging system including a radiographic image processing device according to the present exemplary embodiment is described. FIG. 1 shows a schematic structural diagram of general overall structure of an example of the radiographic imaging system according to the present exemplary embodiment. In a radiographic imaging system 10 according to the present exemplary embodiment, an imaging region of an electronic cassette 12 is plurally divided into division regions, and the radiographic imaging system 10 includes a function that performs serial imaging using the division regions one at a time. Hereinafter, the serial imaging that uses the plural division regions into which the imaging region of the electronic cassette 12 is divided one at a time is referred to as "division imaging".

The radiographic imaging system 10 according to the present exemplary embodiment includes functions for capturing radiographic images in response to operations by users, who are doctors, radiographers and the like, on the basis of instructions (imaging menu selections) inputted from an external system (for example, a radiology information system (RIS)) via a console 20.

The radiographic imaging system 10 according to the present exemplary embodiment also includes functions that enable users to interpret radiographic images, by displaying a captured radiographic image at a display 50 (see FIG. 7) of the console 20 or at a radiographic image interpretation device or the like.

The radiographic imaging system 10 according to the present exemplary embodiment is equipped with the electronic cassette 12, an imaging table 14, a radiation irradiation device 16, the console 20, a user interface (UI) section 22, a console 24, a user interface (UI) section 25, a shielding plate movement section 30, an electronic cassette movement section 32 and a shielding plate 34.

The console 20 acquires imaging menu selections, various kinds of information and the like from an external system (the RIS) or the like via a wireless communications local area network (LAN) or the like. The console 20 includes functions that use the various acquired information to control the electronic cassette 12, the radiation irradiation device 16, the shielding plate movement section 30, the electronic cassette movement section 32 and an image intensifier 36. The console 20 also includes a function that displays captured radiographic images, states of progress of imaging and the like at a display 50 of the UI section 22 (see FIG. 7). The console 20 further includes a function to acquire instructions relating to imaging from the UI section 22.

The image intensifier 36 includes a function that detects radiation X. The image intensifier 36 outputs detection results to the console 20. In the radiographic imaging system 10 according to the present exemplary embodiment, positioning of an imaging subject 18 (a patient or the like) is conducted on the basis of detection results from the image intensifier 36.

The shielding plate movement section 30 includes a function that moves the shielding plate 34 in accordance with control by the console 20 during division imaging. A motor and the like can be mentioned as an example of the shielding plate movement section 30. The shielding plate 34 is formed of a material that does not transmit the radiation X, and includes a window 35 through which the radiation X is allowed to pass. In the radiographic imaging system 10 according to the present exemplary embodiment, during division imaging, the shielding plate 34, which is set on a guide rail, is moved to an imaging position of the imaging table 14 by the shielding plate movement section 30.

The electronic cassette movement section 32 includes a function that, in accordance with control by the console 20, moves the electronic cassette 12 relative to the shielding plate 34 in a direction that is parallel to a plane of imaging of the imaging table 14. A motor and the like can be mentioned as an example of the electronic cassette movement section 32. In the radiographic imaging system 10 according to the present exemplary embodiment, during division imaging, the electronic cassette 12, which is set on a guide rail, is moved by the electronic cassette movement section 32 in accordance with the progress of imaging.

The console 24 includes functions that control the electronic cassette 12. The console 24 also includes functions that display captured radiographic images, states of progress of imaging and the like at a display 54 of the UI section 25 (see FIG. 7). The console 24 further includes a function that acquires instructions relating to imaging from the UI section 25.

The radiation irradiation device 16 is equipped with a vacuum tube. The radiation irradiation device 16 includes a function that irradiates the radiation X from the vacuum tube at an imaging target region of the imaging subject 18 on the imaging table 14, in accordance with control by the console 20.

Radiation X that passes through the imaging subject 18 is irradiated onto the electronic cassette 12, which is retained inside the imaging table 14. The electronic cassette 12 includes functions that generate electric charges in accordance with radiation amounts of the radiation X passing through the imaging subject 18, and that generate image information representing a radiographic image on the basis of the generated charge amounts and output the image information. In the present exemplary embodiment, the image information representing a radiographic image that is outputted by the electronic cassette 12 is inputted to the console 20 and the console 24. In the radiographic imaging system 10 according to the present exemplary embodiment, the electronic cassette 12 itself includes a function that detects the start of an irradiation of radiation (the start of imaging).

Figure 2:
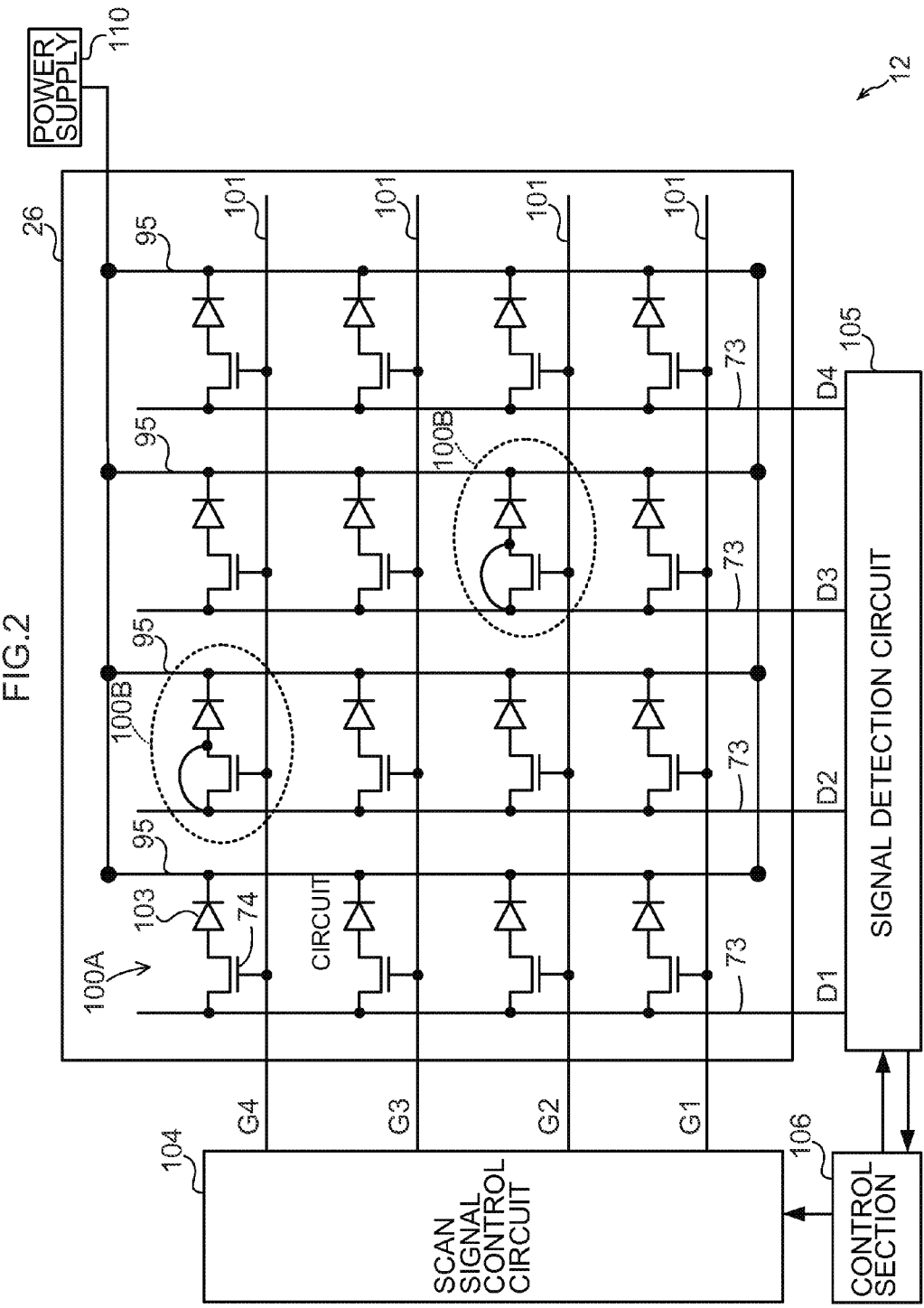
FIG. 2 is a structural diagram showing an example of structure of an electronic cassette in accordance with the first exemplary embodiment.

The general structure of the electronic cassette 12, of a digital radiography (DR) type, according to the present exemplary embodiment, which is illustrated in FIG. 2, is described. In the present exemplary embodiment, a case is described in which the present disclosure is applied to a radiation detector 26 of an indirect conversion type, which temporarily converts radiation such as X-rays or the like to light and then converts the converted light to electric charges. In the present exemplary embodiment, the electronic cassette 12 is equipped with the indirect conversion-type radiation detector 26.

The radiation detector 26 is provided with a plural number of pixels 100 (pixels 100A and 100B, which are described below). Each pixel 100 includes a sensor portion 103 and a thin film transistor (TFT) switch 74. The sensor portion 103 senses light and generates charges, and accumulates the generated charges. The TFT switch 74 is a switching element for reading out the charges accumulated in the sensor portion 103. In the present exemplary embodiment, the sensor portion 103 generates charges when irradiated with the light to which the radiation is converted by a scintillator.

The pixels 100 are plurally arranged in a matrix pattern in one direction (the direction of gate lines in FIG. 2) and a direction intersecting the gate line direction (the direction of signal lines in FIG. 2). In FIG. 2, the arrangement of the pixels 100 is shown simplified; for example, the pixels 100 are arranged 1024 in the gate line direction by 1024 in the signal line direction. In the present exemplary embodiment, a region in which the pixels 100 are arranged is a region in which a radiographic image is captured (generated). This region is referred to as the "imaging region". A surface corresponding with this imaging area at the side of the imaging table 14 at which the imaging subject 18 is disposed is referred to as the "imaging surface".

In the present exemplary embodiment, among the plural pixels 100, pixels for radiographic image capture 100A and pixels for radiation sensing 100B are specified in advance. In FIG. 2, the pixels for radiation sensing 100B are encircled by broken lines. The pixels for radiographic image capture 100A are used for detecting the radiation and generating an image represented by the radiation. The pixels for radiation sensing 100B are pixels that are used to sense radiation, in order to detect the start of an irradiation of radiation and the like. The pixels for radiation sensing 100B are pixels (described in detail herebelow) that output charges even during a charge accumulation period.

Figure 4:
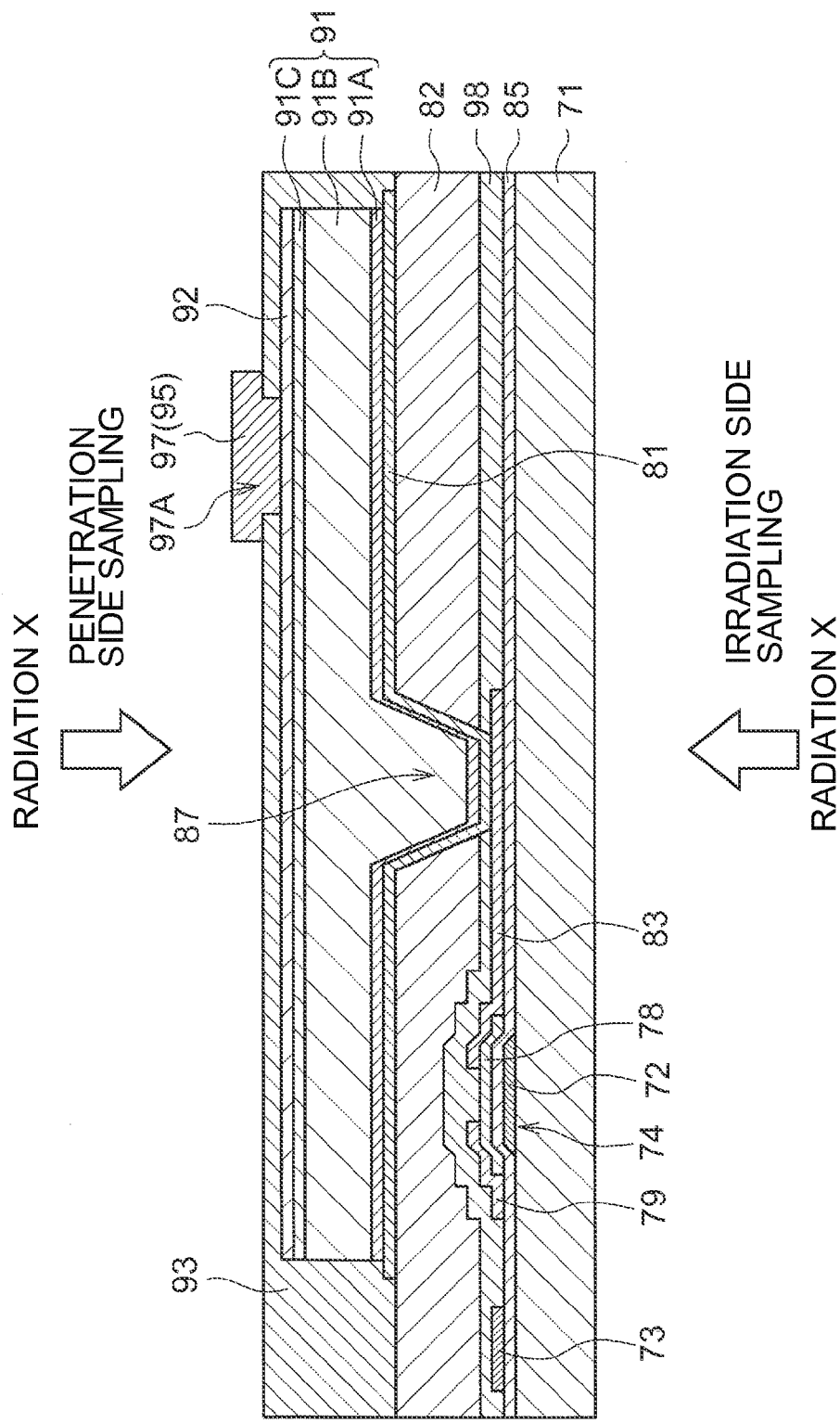
FIG. 4 is a sectional view, cut along line IV-IV, of a pixel for radiographic image capture shown in FIG. 3.

In the radiation detector 26, plural gate lines 101 and plural signal lines 73 are disposed orthogonally to one another on a substrate 71 (see FIG. 4). The gate lines 101 are for turning the TFT switches 74 on and off. The signal lines 73 are for reading out the charges accumulated in the sensor portions 103. In the present exemplary embodiment, one of the signal lines 73 is provided for each pixel row in the one direction, and one of the gate lines 101 is provided for each pixel row in the intersecting direction. For example, in the case in which 1024 by 1024 of the pixels 100 are arranged in the gate line direction and the signal line direction, 1024 each of the signal lines 73 and the gate lines 101 are provided.

In the radiation detector 26, common electrode lines 95 are arranged in parallel with the signal lines 73. One ends and other ends of the common electrode lines 95 are connected in parallel, and a power supply 110 that supplies a predetermined bias voltage is connected to the one ends. The sensor portions 103 are connected to the common electrode lines 95, and the bias voltage is applied to the sensor portions 103 via the common electrode lines 95.

Control signals for switching the TFT switches 74 flow through the gate lines 101. The TFT switches 74 are switched by these control signals flowing in the gate lines 101.

In accordance with the switching states of the TFT switches 74 of the pixels 100, electronic signals corresponding to the charges accumulated in the pixels 100 flow in the signal lines 73. More specifically, when the TFT switch 74 of any of the pixels 100 connected to a signal line 73 is turned on, an electronic signal corresponding to the charge amount accumulated in that pixel 100 flows in that signal line 73.

A signal detection circuit 105 that detects the electronic signals flowing out through the signal lines 73 is connected to the signal lines 73. A scan signal control circuit 104 that outputs control signals to the gate lines 101 for turning the TFT switches 74 on and off is connected to the gate lines 101. FIG. 2 is simplified to show a single signal detection circuit 105 and scan signal control circuit 104. However, for example, the signal detection circuit 105 and the scan signal control circuit 104 may be plurally provided and a predetermined number (for example, 256) of the signal lines 73 or gate lines 101 connected to each signal detection circuit 105 or scan signal control circuit 104. For example, in the case in which 1024 each of the signal lines 73 and the gate lines 101 are provided, four of the scan signal control circuit 104 are provided and each is connected to 256 of the gate lines 101, and four of the signal detection circuit 105 are provided and each is connected to 256 of the signal lines 73.

Figure 6:
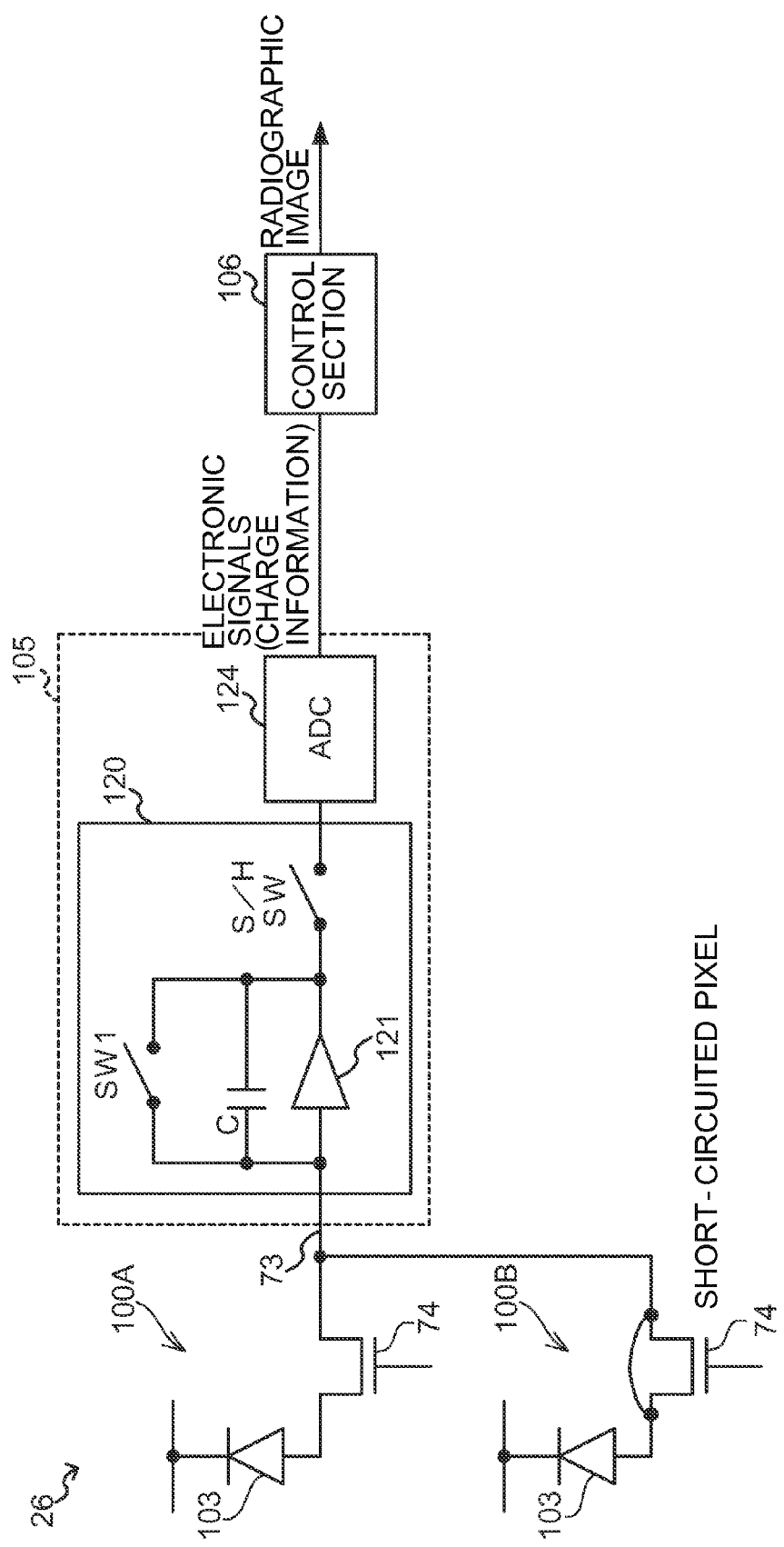
FIG. 6 is a schematic structural diagram of an example of a signal sensing circuit in accordance with the first exemplary embodiment.

For each signal line 73, the signal detection circuit 105 incorporates an amplification circuit 120 that amplifies the inputted electronic signals (see FIG. 6). In the signal detection circuit 105, the electronic signals inputted from the signal lines 73 are amplified by the amplification circuits 120 and converted to digital signals by an analog/digital converter (ADC) (described in more detail below).

A control section 106 is connected to the signal detection circuit 105 and the scan signal control circuit 104. The control section 106 applies predetermined processing such as noise removal and the like to the digital signals converted at the signal detection circuit 105, outputs control signals indicating signal detection timings to the signal detection circuit 105, and outputs control signals indicating scan signal output timings to the scan signal control circuit 104.

The control section 106 according to the present exemplary embodiment is provided with a CPU, ROM and RAM, and a non-volatile storage section formed with flash memory or the like. The control section 106 executes a program memorized in the RAM with the CPU, and carries out control for capturing a radiographic image. The control section 106 applies processing to interpolate image data for the pixels for radiation sensing 100B (interpolation processing) to the image data to which the above-mentioned predetermined processing has been applied, to generate an image representing the irradiated radiation. That is, the control section 106 generates the image represented by the irradiated radiation by interpolating image data for the pixels for radiation sensing 100B on the basis of the image data that has been subjected to the above predetermined processing.

Figure 3:
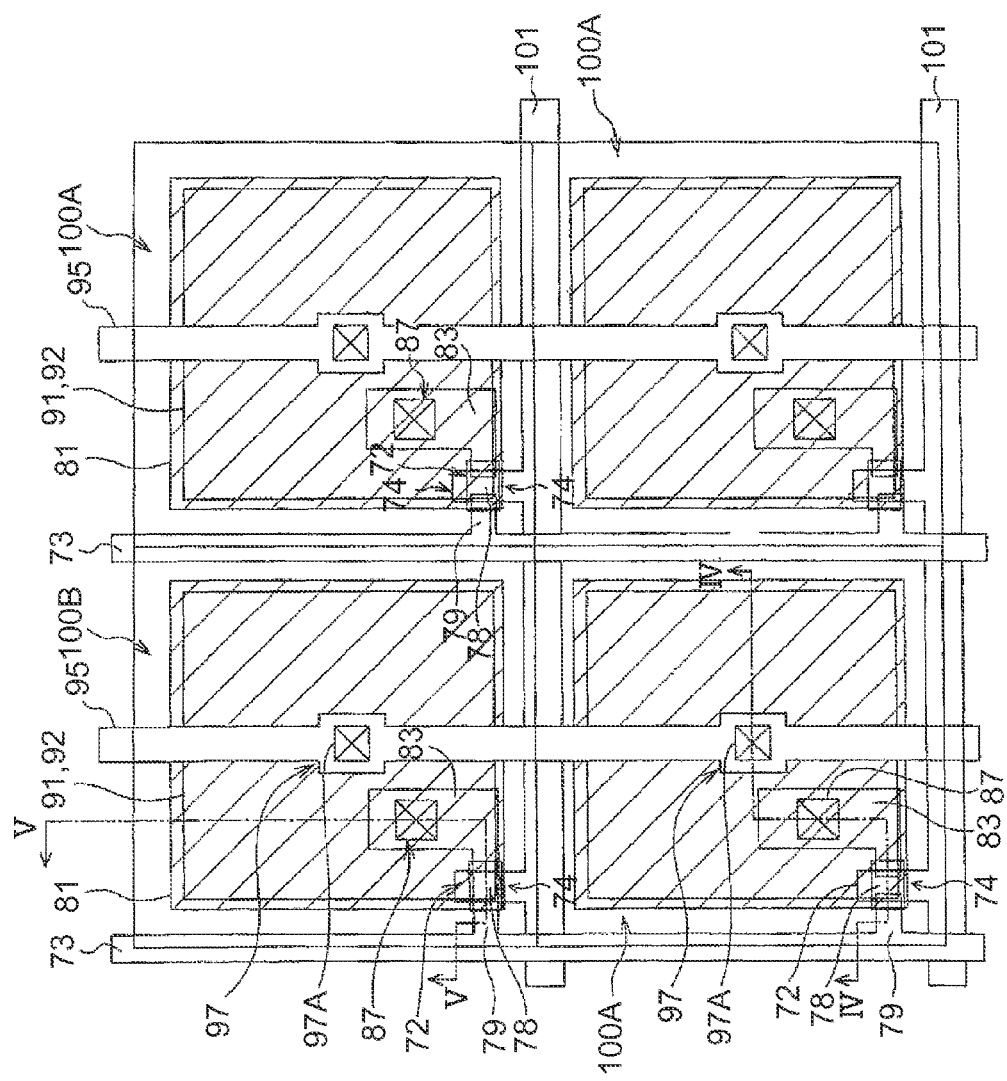
FIG. 3 is a plan view showing an example of structure of an indirect conversion-type radiation detector in accordance with the first exemplary embodiment.
Figure 5:
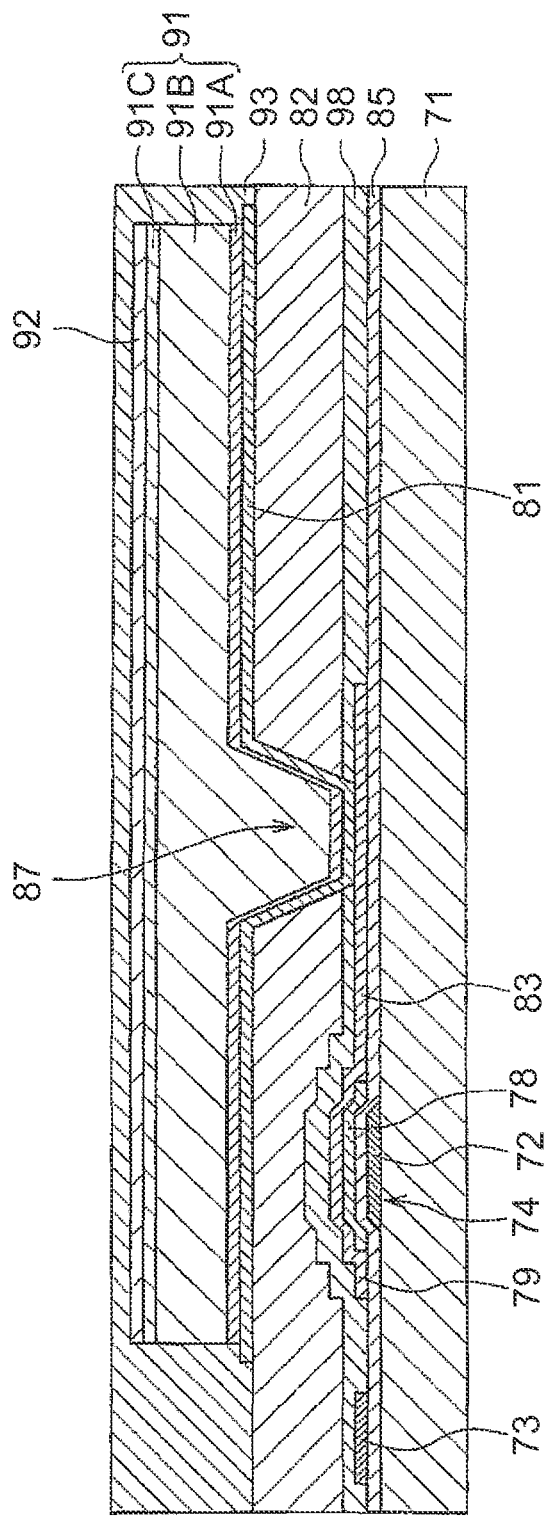
FIG. 5 is a sectional view, cut along line V-V, of a pixel for radiation sensing shown in FIG. 3.

FIG. 3 shows a plan view illustrating an example of structure of the indirect conversion-type radiation detector 26 according to the present exemplary embodiment. FIG. 4 shows a sectional view of one of the pixels for radiographic image capture 100A taken along line IV-IV in FIG. 3, and FIG. 5 shows a sectional view of one of the pixels for radiation sensing 100B taken along line V-V in FIG. 3.

As shown in FIG. 4, in each pixel for radiographic image capture 100A of the radiation detector 26, the gate line 101 (see FIG. 3) and a gate electrode 72 are formed on the substrate 71, which is formed of non-alkaline glass or the like, and the gate line 101 is connected with the gate electrode 72 (see FIG. 3). A wiring layer in which the gate line 101 and the gate electrode 72 are formed (hereinafter, this wiring layer is referred to as the "first signal wiring layer") is formed using aluminium or copper, or a layered film whose principal constituent is aluminium or copper, but is not limited to these.

An insulation layer 85 is formed over the whole area of the first signal wiring layer. A portion of the insulation layer 85 that is disposed over the respective gate electrode 72 is employed as a gate insulation layer of the TFT switch 74. The insulation layer 85 is formed of, for example, $SiN_x$ or the like, and is formed by, for example, chemical vapor deposition (CVD) film formation.

A semiconductor active layer 78 is formed on the insulation layer 85 in a pattern of islands over the gate electrodes 72. The semiconductor active layer 78 is the channel portion of each TFT switch 74. The semiconductor active layer 78 is formed of, for example, a film of amorphous silicon.

Source electrodes 79 and drain electrodes 83 are formed in a layer thereabove. The signal lines 73 are formed together with the source electrodes 79 and the drain electrodes 83 in a wiring layer in which the source electrodes 79 and the drain electrodes 83 are formed. The source electrodes 79 are connected to the signal lines 73 (see FIG. 3). The wiring layer in which the source electrodes 79, drain electrodes 83 and signal lines 73 are formed (hereinafter this wiring layer is referred to as the "second signal wiring layer") is formed using aluminium or copper, or a layered film whose principal constituent is aluminium or copper, but is not limited to these. A doped semiconductor layer, of amorphous silicon doped with impurities or the like, is formed between the source electrodes 79 and drain electrodes 83 and the semiconductor active layer 78. The TFT switches 74 for switching are structured by these parts. Note that the source electrode 79 and the drain electrode 83 may be exchanged depending on the polarity of the charges to be collected and accumulated by a lower electrode 81 of the TFT switch 74, which is described below.

A TFT protection layer 98 is formed to cover the second signal wiring layer over substantially the whole area of a region of the substrate 71 in which the pixels 100 are provided (substantially the whole of the region). The TFT protection layer 98 is for protecting the TFT switches 74 and signal lines 73 and the like. The TFT protection layer 98 is formed of, for example, $SiN_x$ or the like, and is formed by, for example, CVD film formation.

An interlayer insulation film 82 is formed as a coating on the TFT protection layer 98. This interlayer insulation film 82 is formed with a film thickness of 1 to 4 µm of a photosensitive organic material with low permittivity (relative permittivity $\epsilon r=2$ to 4) (for example, a positive-type photosensitive acrylic resin such as a material in which a naphthoquinone diazide-based positive-type photosensitizer is mixed into a base polymer formed of a copolymer of methacrylic acid and glycidyl methacrylate, or the like).

In the radiation detector 26 according to the present exemplary embodiment, a capacitance between metals disposed in a layer above and the layer below the interlayer insulation film 82 is kept low by the interlayer insulation film 82. In addition, this kind of material generally functions as a flattening film, and provides an effect of flattening over steps in the layers therebelow. In the radiation detector 26 according to the present exemplary embodiment, contact holes 87 are formed at positions of the interlayer insulation film 82 and the TFT protection layer 98 that oppose the drain electrodes 83.

The lower electrodes 81 of the sensor portions 103 are formed on the interlayer insulating film 82 so as to cover the pixel regions and fill in the contact holes 87, and the lower electrodes 81 are connected with the drain electrodes 83 of the TFT switches 74. If semiconductor layers 91, which are described below, have a thickness of around 1 µm, the material of the lower electrodes 81 is hardly limited at all provided the lower electrodes 81 are conductive. Therefore, there is no problem provided the lower electrodes 81 are formed using a conductive metal such as an aluminium-based material, ITO (indium tin oxide) or the like.

If the film thickness of the semiconductor layers 91 is small (around 0.2-0.5 µm), light is insufficiently absorbed by the semiconductor layers 91. Therefore, in order to prevent an increase in leakage currents caused by illumination of light onto the TFT switches 74, it is preferable if the semiconductor layers 91 are an alloy or layered film with a light-blocking metal as a principal constituent thereof.

The semiconductor layers 91, which function as photodiodes, are formed on the lower electrodes 81. In the present exemplary embodiment, PIN-architecture photodiodes, in which an n+ layer, an i layer and a p+ layer are layered (n+ amorphous silicon, amorphous silicon, and p+ amorphous silicon), are employed as the semiconductor layers 91. The semiconductor layers 91 are formed by an n+ layer 91A, an i layer 91B and a p+ layer 91C being layered in this order from the lowest layer. The i layer 91B generates charges (pairs of free electrons and free holes) when illuminated with light. The n+ layer 91A and the p+ layer 91C function as contact layers and electronically connect the lower electrodes 81 and upper electrodes 92, which are described below, with the i layer 91B.

The upper electrodes 92 are respectively individually formed over the semiconductor layers 91. A material with high light transmissivity such as, for example, ITO, IZO (indium zinc oxide) or the like is used for the upper electrodes 92. In the radiation detector 26 according to the present exemplary embodiment, each sensor portion 103 includes the upper electrode 92, the semiconductor layers 91 and the lower electrode 81.

A coating-form interlayer insulation film 93 is formed over the interlayer insulation film 82, the semiconductor layers 91 and the upper electrodes 92, so as to cover the semiconductor layers 91 with openings 97A being formed at portions that correspond with the upper electrodes 92.

The common electrode lines 95 are formed over the interlayer insulation film 93, of aluminium, copper, or an alloy or layered film with aluminium or copper as a principal constituent. Contact pads 97 are formed on the common electrode lines 95 near the openings 97A. The contact pads 97 are electronically connected with the upper electrodes 92 through the openings 97A in the interlayer insulation film 93.

In contrast, at each pixel for radiation sensing 100B of the radiation detector 26, as shown in FIG. 5, the TFT switch 74 is formed such that the source electrode 79 and the drain electrode 83 are in contact. That is, in the pixel 100B, the source and drain of the TFT switch 74 are short-circuited. Therefore, charges collected at the lower electrode 81 of the pixel 100B flow into the signal line 73 regardless of the switching state of the TFT switch 74.

A scintillator, which is a radiation conversion layer, is provided on the radiation detector 26 that is formed in this manner. If required, a protective film is formed of an insulating material with low light absorption, and the scintillator is adhered to the surface thereof using an adhesive resin with low light absorption. The scintillator may also be formed by vacuum vapor deposition. It is desirable if the scintillator generates fluorescent light with a relatively wide wavelength range, such that light in a wavelength range that can be absorbed is produced. This kind of scintillator may include CsI:Na, $CaWO_4$, $YTaO_4$:Nb, BaFX:Eu (in which X is Br or Cl), LaOBr:Tm, GOS or the like. Specifically, in a case in which X-rays are used as the radiation X and imaged, it is preferable to include cesium iodide (CsI). It is particularly preferable to use cesium iodide with thallium added thereto (CsI:Tl), which has a light emission spectrum with a wavelength range of 400 nm to 700 nm when X-rays are irradiated thereon, or CsI:Na or the like. CsI:Tl has a light emission peak wavelength of 565 nm, in the visible light region. If a scintillator containing CsI is to be used, it is preferable to use a scintillator that is formed with a rectangular slice-shaped columnar crystal structure by vacuum vapor deposition.

In a case in which, as shown in FIG. 4, the radiation X is irradiated from the side of the radiation detector 26 at which the semiconductor layers 91 are formed and the radiation detector 26 acquires the radiographic image with the TFT substrate that is provided at a rear face side relative to the face at which the radiation X is incident, which is referred to as penetration side sampling (PSS), light is more strongly emitted from the side of the scintillator provided at the semiconductor layers 91 that is at the upper face side in FIG. 4. In a case in which the radiation X is irradiated from the side of the radiation detector 26 at which the TFT substrate is formed and the radiation detector 26 acquires the radiographic image with the TFT substrate that is provided at a front face side relative to the face at which the radiation X is incident, which is referred to as irradiation side sampling (ISS), radiation X that has passed through the TFT substrate is incident on the scintillator and light is more strongly emitted from the side of the scintillator at which the TFT substrate is disposed. Charges are produced by the light emitted from the scintillator to the sensor portions 103 of the pixels 100 provided at the TFT substrate. Therefore, in a case in which the radiation detector 26 is of an ISS type, light emission positions of the scintillator are closer to the TFT substrate than in a case in which the radiation detector 26 is of a PSS type. As a result, the resolution of the radiographic images obtained by imaging is higher.

The radiation detector 26 is not limited to the structures shown in FIG. 3 to FIG. 5; various modifications are possible. For example, in a case of penetration side sampling, probabilities of the radiation X reaching the radiation detector 26 are lower. Therefore, instead of the structure described above, another imaging component such as a complementary metal oxide semiconductor (CMOS) image sensor or the like with low resistance to the radiation X may be combined with the TFTs. Further, a charge-coupled device (CCD) image sensor that shifts and transfers charges in accordance with shift pulses that correspond to the TFT gate signals may be substituted.

As another example, a flexible substrate may be used. A flexible substrate in which ultra-thin plate glass formed by a recently developed float process is used as a base material may be employed, and is preferable in terms of improving transmissivity of the radiation.

Now, general structure of the signal detection circuit 105 according to the present exemplary embodiment is described. FIG. 6 is a schematic structural diagram of an example of the signal detection circuit 105 according to the present exemplary embodiment. The signal detection circuit 105 of the present exemplary embodiment is equipped with the amplification circuits 120 and an analog/digital converter (ADC) 124. The amplification circuits 120 are provided one for each of the signal lines 73. That is, the signal detection circuit 105 is equipped with plural amplification circuits 120 in the same number as the number of signal lines 73 in the radiation detector 26.

Each amplification circuit 120 is structured as a charge amplification circuit and is provided with an amplifier 121, such as an operational amplifier or the like, a capacitor C that is connected in parallel with the amplifier 121, and a switch for charge resetting SW1 that is connected in parallel with the amplifier 121.

When the switch for charge resetting SW1 of the amplification circuit 120 is in the off state, charges (electronic signals) are read out by the TFT switch 74 of a pixel 100, the charges read out by the TFT switch 74 are accumulated at the capacitor C, and a voltage value outputted from the amplifier 121 increases in accordance with the accumulated charge amount.

The control section 106 applies charge reset signals to the switches for charge resetting SW1 and performs control to turn the switches for charge resetting SW1 on and off. When a switch for charge resetting SW1 is in the on state, the input side and output side of that amplifier 121 are short-circuited together and charges are discharged from the capacitor C.

The ADC 124 includes a function that converts electronic signals that are analog signals inputted from the amplification circuits 120 to digital signals, when sample-and-hold (S/H) switches SW are in the on state. The ADC 124 sequentially outputs the electronic signals that have been converted to digital signals to the control section 106.

The electronic signals outputted from all the amplification circuits 120 provided in the signal detection circuit 105 are inputted to the ADC 124 according to the present exemplary embodiment. That is, the signal detection circuit 105 according to the present exemplary embodiment is equipped with a single ADC 124 regardless of the number of amplification circuits 120 (and signal lines 73).

In the present exemplary embodiment, electronic signals (charge information) from the signal lines 73 to which the pixels for radiation sensing 100B are connected (in the case shown in FIG. 2, one or both of D2 and D3, for example, D2) are detected by the amplification circuits 120 of the signal detection circuit 105. The control section 106 compares the values of the digital signals converted by the signal detection circuit 105 with a pre-specified detection threshold value, and detects whether or not radiation has been irradiated from whether or not the electronic signals are above the threshold value. That is, the control section 106 of the electronic cassette 12 detects irradiations of radiation without needing control signals from outside the electronic cassette 12 (for example, from the console 20 or the console 24). The detection of the start of an irradiation of radiation by the control section 106 is not limited to comparison with a detection threshold value. For example, a detection circuit or the like may perform the detection on the basis of pre-specified conditions.

The meaning of the term "detection" of electronic signals as used in the present exemplary embodiment includes sampling of the electronic signals.

As described above, the radiographic imaging system 10 according to the present exemplary embodiment includes a function that performs division imaging. In the electronic cassette 12 according to the present exemplary embodiment, after imaging of all division regions has been completed, charges are read out from all of the pixels 100 together. The TFT switches 74 that read out the charges from the pixels are kept turned off from the start of the first stage of division imaging until the end of the final stage of division imaging. Therefore, charges that are caused by dark currents (hereinafter referred to simply as the "dark current") are accumulated in the pixels 100. The dark current affects the image quality of a captured radiographic image. As the dark current increases, image quality deteriorates. Therefore, a permissible value of the dark current (of charge amounts) is determined (see FIG. 11). The charge accumulation period is limited in the electronic cassette 12 in order to ensure that the dark current does not exceed the permissible value. In a cassette of a computed radiography (CR) type, in contrast to an electronic cassette of the DR type, the dark current does not cause any problem. Therefore, imaging durations (an accumulation period), irradiation durations of the radiation X and the like would not be subject to limitations due to the dark current.

That is, in the electronic cassette 12, imaging of all the division regions must be carried out within a limit duration of the accumulation period. Quantities of the dark current vary in accordance with conditions such as irradiation amounts of the radiation X, temperature and the like. However, in the electronic cassette 12 according to the present exemplary embodiment, as an example, the limit duration of the accumulation period is set to 10 seconds.

Therefore, the accumulation period each time division imaging is performed is limited. Because it is difficult for a user to perceive accumulation states of charges in the radiation detector 26, there may be cases in which accumulation durations cannot be identified and division imaging cannot be performed appropriately. In order to prevent such cases, in the radiographic imaging system 10 according to the present exemplary embodiment, a state of progress of the imaging is displayed so as to include information relating to remaining imaging. Thus, a remaining duration of the accumulation period (hereinafter referred to as the "remaining accumulation duration"), a number of remaining irradiations, irradiation timings and the like are reported to a user.

Figure 7:
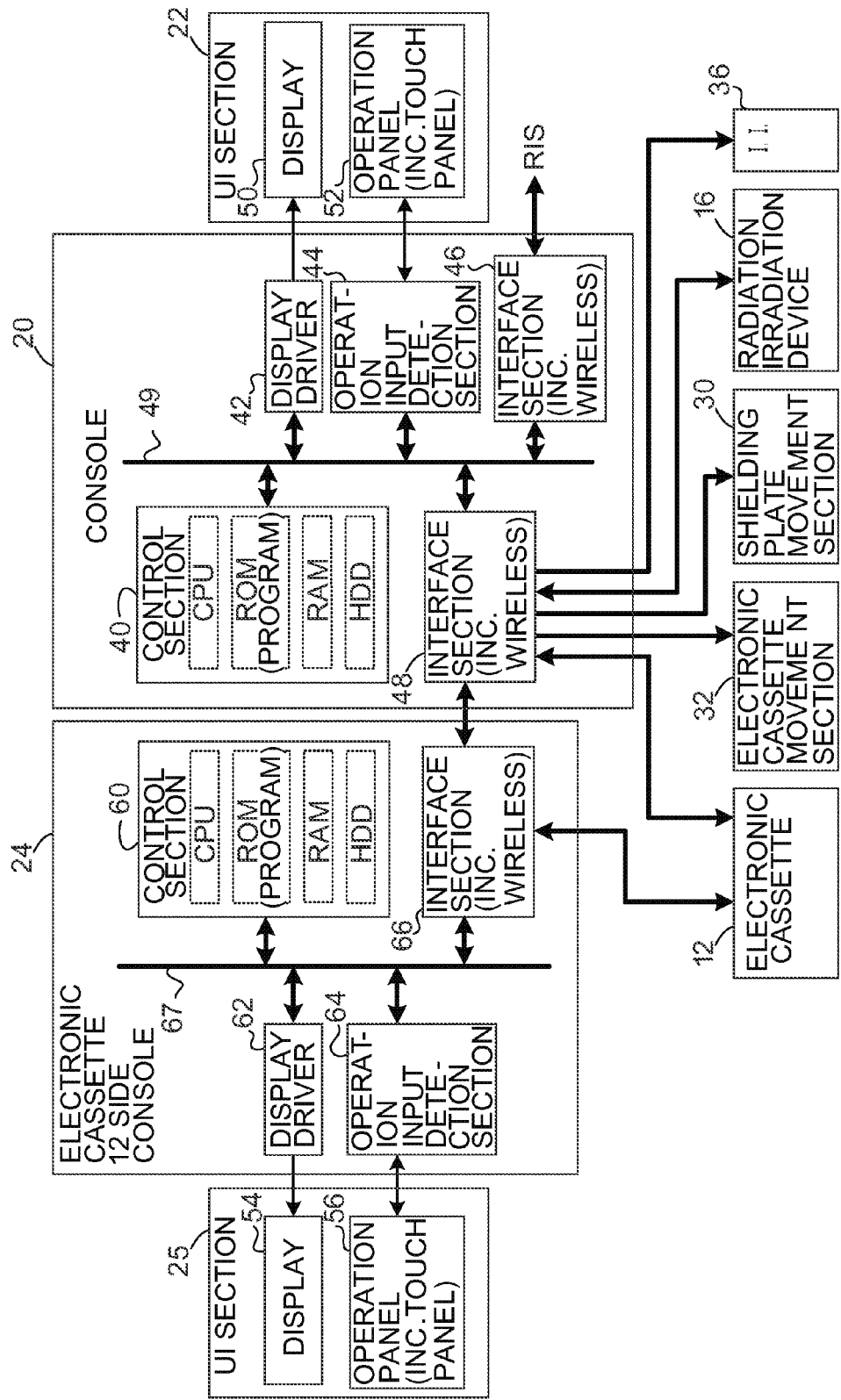
FIG. 7 is a functional block diagram for describing an example of functions relating to the display of a state of progress during division imaging by a console at the electronic cassette side in accordance with the first exemplary embodiment.

As an example, in the radiographic imaging system 10 according to the present exemplary embodiment, the console 24 at the electronic cassette 12 side causes the state of progress of the imaging to be displayed at the display 54 of the UI section 25. FIG. 7 shows a functional block diagram for describing an example of functions relating to the display of the state of progress during division imaging by the console 24. In the radiographic imaging system 10 according to the present exemplary embodiment, a control section 60 of the console 24 functions as an imaging control section and as a display control section.

The console 20 that controls the radiographic imaging system 10 according to the present exemplary embodiment as a whole is a server computer. The console 20 is provided with a control section 40, a display driver 42, an operation input detection section 44, an interface (I/F) section 46 and an interface section 48.

The control section 40 includes functions that control overall operations of the console 20. The control section 40 according to the present exemplary embodiment includes functions that control imaging (including division imaging) by controlling the radiographic imaging system 10 as a whole. The control section 40 is provided with a CPU, ROM, RAM and an HDD (hard disk drive). The CPU includes functions that control overall operations of the console 20. Various programs including a control program to be used at the CPU and suchlike are pre-memorized in the ROM. The RAM includes functions that temporarily store various kinds of data. The HDD includes functions that store and retain various kinds of data.

The display driver 42 includes functions that control the display of various kinds of information at the display 50 of the UI section 22. The display 50 according to the present exemplary embodiment includes functions that display imaging menus, captured radiographic images and the like. The operation input detection section 44 includes functions that detect operation states of an operation panel 52 of the UI section 22. The operation panel 52 is for the user to input operation instructions in relation to the imaging of radiographic images. The operation panel 52 according to the present exemplary embodiment includes, for example, a touch panel, a touch pen, plural buttons and a mouse, or the like. In a case in which the operation panel 54 is structured as a touch panel, it may be the same unit as the display 50.

The interface section 46 of the console 20 includes a function that exchanges various kinds of information with the RIS by one or both of wireless communications and wired communications. The interface section 48 of the console 20 includes functions that exchange various kinds of information with the electronic cassette 12, the radiation irradiation device 16, the console 24, the shielding plate movement section 30, the electronic cassette movement section 32 and the image intensifier 36 by one or both of wireless communications and wired communications.

The control section 40, the display driver 42, the operation input detection section 44, the interface section 46 and the interface section 48 are connected to be able to transfer information and the like to one another via a bus 49, which is a system bus, a control bus or the like.

The console 24 at the electronic cassette 12 side is a server computer. The console 24 is provided with the control section 60, a display driver 62, an operation input detection section 64 and an interface section 66.

The control section 60 includes functions that control overall operations of the console 24. The control section 60 is provided with a CPU, ROM, RAM and an HDD. The CPU includes functions that control overall operations of the console 24. Various programs including a control program to be used at the CPU and suchlike are pre-memorized in the ROM. The RAM includes functions that temporarily store various kinds of data. The HDD includes functions that store and retain various kinds of data.

The display driver 62 includes functions that control the display of various kinds of information at the display 54 of the UI section 25. The display 54 according to the present exemplary embodiment includes a function that displays information relating to imaging (the state of progress of the imaging) and the like. The operation input detection section 64 includes functions that detect operation states of an operation panel 56 of the UI section 25. The operation panel 56 is for users to input operation instructions in relation to the imaging of radiographic images. The operation panel 56 according to the present exemplary embodiment includes, for example, a touch panel, a touch pen, plural buttons and a mouse, or the like. In a case in which the operation panel 56 is structured as a touch panel, it may be the same unit as the display 54.

The interface section 66 of the console 24 includes a function that exchanges various kinds of information with the electronic cassette 12 and the console 20 by one or both of wireless communications and wired communications.

The control section 60, the display driver 62, the operation input detection section 64 and the interface section 66 are connected to be able to transfer information and the like to one another via a bus 67, which is a system bus, a control bus or the like.

Now, the flow of division imaging processing, which is control that is performed at the console 24 during division imaging, is described. FIG. 8 shows a flowchart depicting an example of the flow of the division imaging processing. FIG. 9 shows a descriptive diagram for describing the division imaging by the radiographic imaging system 10. As an example, FIG. 9 illustrates a case of esophagography of the imaging subject 18. Herebelow, as an example, a case is described in detail in which the number of division regions (the number of division imaging stages) is five.

In the present exemplary embodiment, a case is described in which the user instructs timings of irradiation of the radiation X for each division region. This irradiation instruction is performed through the operation panel 52 of the UI section 22 or the operation panel 56 of the UI section 25.

The radiographic imaging system 10 performs division imaging in a case in which division imaging is instructed by the user, a case in which division imaging is instructed from an imaging menu, and the like. In the radiographic imaging system 10, the user performs instructions relating to division imaging through the operation panel 52 of the UI section 22 or the operation panel 56 of the UI section 25.

In the division imaging, first, in order to perform positioning in preparation for imaging, the console 20 moves the electronic cassette 12 with the electronic cassette movement section 32 and moves the shielding plate 34 with the shielding plate movement section 30, moving the electronic cassette 12 and the shielding plate 34 away from the imaging surface of the imaging table 14. The user positions the imaging subject 18 at the imaging table 14, referring to detection results from the image intensifier 36. During this positioning, the radiation X is irradiated from the radiation irradiation device 16 for shorter durations and in smaller amounts than in a case of capturing a radiographic image. When this positioning is complete, the imaging subject 18 swallows a radiocontrast agent (for example, barium) and the preparation for imaging is complete.

When the division imaging is to be carried out, the console 20 notifies the console 24 and the electronic cassette 12 to switch into a division imaging mode. When the console 24 switches into the division imaging mode, the division imaging processing shown in FIG. 8 starts. The division imaging processing is executed by a program memorized in the ROM of the control section 60 being executed.

In step S100, the control section 60 acquires the number of divisions. The method for acquiring the number of divisions may be acquisition from the console 20 controlling the radiographic imaging system 10 as a whole or may be acquisition from an imaging menu, and is not particularly limited.

Then, in step S102, the control section 60 makes a determination as to whether division imaging is possible. In the electronic cassette 12, a charge accumulation duration required for a single image capture (for one radiographic image) to capture a radiographic image (which may be a division image) that is suitable for interpretation is set. Accordingly, an accumulation duration required for imaging of all the division regions (hereinafter referred to as the total accumulation duration) is determined by the number of divisions. However, because the dark current occurs in the radiation detector 26 as mentioned above, a limit duration of the accumulation durations is also set. In the present exemplary embodiment, if the total accumulation duration exceeds the limit duration, there is a risk that it may not be possible to carry out suitable imaging, and it is accordingly determined that division imaging is not possible.

A minimum size of division regions required to image the whole of an imaging target (region of interest) of the imaging subject 18 is set in accordance with the type of imaging. The sizes of the division regions may all be the same or may be different. How the sizes of the division regions are set may be pre-specified in accordance with the type of imaging, or may be instructed by the user. In a case in which the user instructs a size of the division regions, the control section 60 according to the present exemplary embodiment makes a determination that division imaging is not possible if the size is smaller than the minimum required size. Alternatively, in a case in which the user instructs a number of divisions, the control section 60 determines a size of the division regions, and makes a determination that division imaging is not possible if the determined size is smaller than the minimum required size. In the radiographic imaging system 10 according to the present exemplary embodiment, in a case in which no particular instruction is given, the size of the division regions is determined by dividing the imaging region by the number of divisions. When the size of the division regions has been determined, the size of the window 35 of the shielding plate 34 is adjusted to match the determined size. In the radiographic imaging system 10 according to the present exemplary embodiment, the size of the window 35 is adjustable.

If the division regions include a division region that does not contain any of the pixels for radiation sensing 100B of the radiation detector 26, it may not be possible to detect the radiation X being irradiated at that division region. Therefore, if it is determined that the pixels for radiation sensing 100B are not present in a division region, the control section 60 makes a determination that division imaging is not possible. A method for determining whether the pixels for radiation sensing 100B are present in a division region is not particularly limited. For example, the positions of the pixels for radiation sensing 100B may be memorized in advance and the determination made by whether or not these positions are included in the division regions. As a further example, division numbers or division region sizes corresponding to the positions of the pixels for radiation sensing 100B may be set in advance and the determination made by comparing the same with a division number or division region size instructed by the user. It is preferable if the radiation detector 26 has a structure such that the pixels for radiation sensing 100B are disposed in division regions that are anticipated in accordance with types of imaging and the like, such that the sizes and numbers of the division regions are limited as little as possible by the arrangement of the pixels for radiation sensing 100B.

If it is determined that division imaging is not possible, the control section 60 proceeds to step S104, carries out error processing, and ends the present processing. The error processing is not particularly limited provided the processing reports to the user that the division is not possible and that a radiographic image that is at least suitable cannot be obtained. A method of reporting may be, for example, display at the display 54 of a message prompting reconsideration of the division number, the sizes of the divisions, the irradiation amounts of the radiation X and the like, or the like. The user receiving this report may reconsider the division number, the sizes of the divisions, the irradiation amounts of the radiation X and the like, and may instruct the execution of division imaging again.

On the other hand, if it is determined that division imaging is possible, the control section 60 proceeds to step S106. It is preferable if, in the case in which it is determined that division imaging is possible, the user is notified that the division imaging is possible and that the division imaging will be executed.

The processing of steps S100 to S104 may be performed before the above-described preparation for imaging, after the preparation for imaging, or in parallel with the preparation. Performing the processing before the preparation is preferable in regard to suppressing radiation exposure of the user.

In step S106, the control section 60 makes a determination as to whether the user has given an irradiation instruction. If no irradiation instruction has been received, the control section 60 goes into a standby state. If an irradiation instruction has been received, the control section 60 proceeds to step S108 and starts the first stage of the division imaging.

As shown in FIG. 9, in the first stage of the division imaging, a division region A is set at a position corresponding with the region of the window 35 of the shielding plate 34. When the radiation X is irradiated from the radiation irradiation device 16, the radiation X passing through the imaging subject 18 is irradiated onto the division region A.

In step S108, the control section 60 commands the control section 106 of the electronic cassette 12 to turn off all of the TFT switches 74 in the radiation detector 26 of the electronic cassette 12 and start the accumulation of charges. In response to this command, the control section 106 outputs control signals through the scan signal control circuits 104 to the gate lines 101 to turn the TFT switches 74 off. In accordance with these control signals, in the pixels for radiographic image capture 100A, the drain electrodes 83 and source electrodes 79 are not shorted together, and therefore charges collected at the lower electrodes 81 are accumulated. In contrast, in the pixels for radiation sensing 100B, because the drain electrodes 83 and source electrodes 79 are shorted together, the charges collected at the lower electrodes 81 flow out to the signal lines 73.

Then, in step S110, the control section 60 starts a display of the state of progress of the imaging at the display 54. FIG.

Figure 10A:
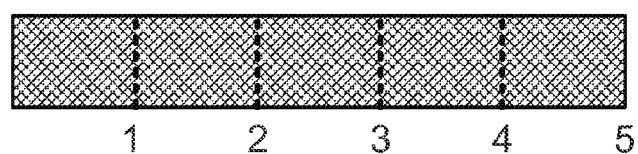
FIG. 10A to FIG. 10D are descriptive diagrams describing a concrete example of the display of the state of progress of the imaging.
Figure 10B:
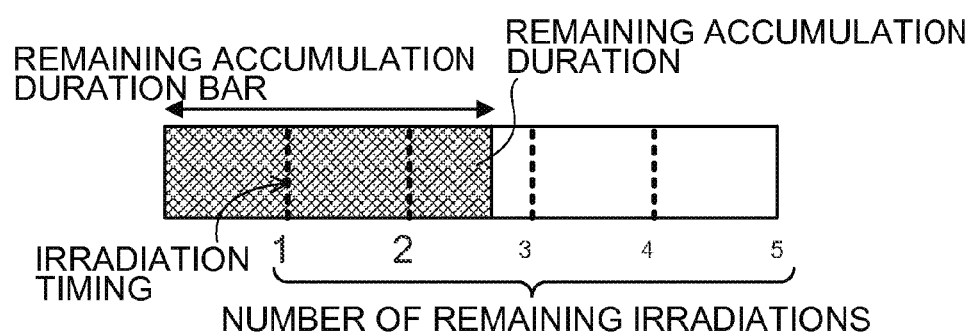
Figure 10C:
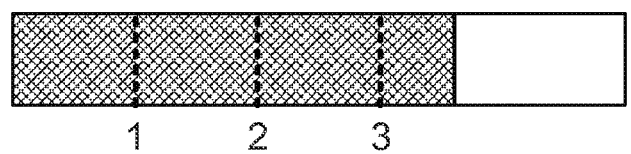
Figure 10D:
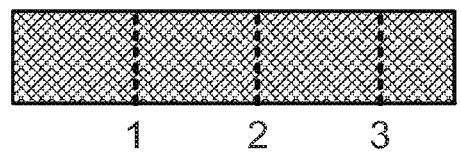

10A to FIG. 10D show examples of the display of the state of progress of the imaging. FIG. 10A shows the state of progress of the imaging that is displayed at the display 54 when the display starts. The display of the state of progress of the imaging is not limited to the displays illustrated in FIG. 10A to FIG. 10D provided the display, in order to display the state of progress of the imaging, reports to the user information relating to remaining imaging.

In the examples shown in FIG. 10A to FIG. 10D, a remaining accumulation duration bar representing the remaining accumulation duration, digits representing numbers of remaining irradiations, and marks representing irradiation timings (the broken lines in FIG. 10A to FIG. 10D) are displayed. The remaining accumulation duration bar represents the remainder of the charge accumulation duration for the whole of the radiation detector 26. As shown in FIG. 10B to FIG. 10D, the remaining accumulation duration bar shortens as the imaging duration (the charge accumulation duration) passes. The digits representing the numbers of remaining irradiations each indicate a number of remaining times the radiation X is to be irradiated at the electronic cassette 12 (the radiation detector 26). Each time the user instructs an irradiation, the number is counted down. The marks representing irradiation timings prompt the user to instruct the irradiations of the radiation X.

In step S112, the control section 60 shortens the remaining accumulation duration bar displayed at the display 54 in correspondence with the passing of the imaging duration.

When the division imaging for division region A, which is the first stage of the division imaging, is complete, the irradiation of the radiation X is stopped by control from the console 20 and the electronic cassette 12 moves. As illustrated in FIG. 9, for the second stage of division imaging, a division region B is set at the position corresponding with the region of the window 35 of the shielding plate 34. In the electronic cassette 12, reading of charges is not performed for each division image. Therefore, the accumulation of charges in the radiation detector 26 is maintained through this period.

In step S114, the radiation irradiation device 16 makes a determination as to whether there is an irradiation instruction from the user. If no irradiation instruction has been received, the control section 60 returns to step S112 and continues to shorten the remaining accumulation duration bar.

When the remaining accumulation duration bar shortens and passes over the broken line representing an irradiation timing, the user recognizes that this is an irradiation timing and gives an irradiation instruction. If an irradiation instruction is received at the control section 60, the control section 60 proceeds to step S116 and starts the second or subsequent stage of division imaging.

Then in step S116, the control section 60 updates the display of the state of progress of the imaging that is displayed at the display 54. In the present exemplary embodiment, in order to show the state of progress of the imaging clearly, as well as the remaining accumulation duration bar being shortened, the display of the state of progress of the imaging is updated each time a stage of division imaging is completed. FIG. 10B to FIG. 10D show display examples of an updated display of the state of progress of the imaging. FIG. 10B shows a case during the third stage of division imaging in a total of five stages of division imaging, with two stages of division imaging remaining.

FIG. 10B and FIG. 10C show cases in which information relating to the stages of division imaging that have already been completed is displayed. FIG. 10B shows a case in which the numbers of remaining irradiations are prominently displayed (large) in the state in which the display starts, and the digits corresponding with the numbers of remaining irradiations are made relatively less prominent (smaller) for irradiations that have already been completed. FIG. 10C shows a case in which the numbers of remaining irradiations are not displayed for irradiations that have already been completed, with digits only being displayed for the numbers of irradiations that still remain. FIG. 10D shows a case in which only information relating to remaining stages of division imaging is displayed.

Then, in step S118, the control section 60 makes a determination as to whether operation is proper, that is, whether the division imaging is being conducted appropriately. The control section 60 according to the present exemplary embodiment makes the determination as to whether operation is proper on the basis of electronic signals detected from the pixels for radiation sensing 100B that correspond to the division region of the electronic cassette 12 that is currently performing division imaging. For example, if the electronic cassette 12 has not moved, electronic signals are not detected or the electronic signals do not change over time. In such a case, the control section 60 determines that operation is not proper. However, because charge amounts generated in the radiation detector 26 increase as the imaging duration passes because of the dark current, electronic signals increase. FIG. 11 shows a descriptive diagram for describing the increase in charge amounts with the accumulation duration due to the dark current Therefore, it is preferable to set a standard (a threshold value) for determining whether or not operation is proper by taking account of the dark current, in accordance with the number of stages of division imaging and the passage of time from the start of the division imaging.

If it is determined that operation is not proper, the control section 60 proceeds to step S120, performs predetermined error processing, and ends the present processing. For example, although the error processing is not particularly limited, it is preferable to include processing that reports to the user that a determination has been made that operation is not proper. In addition, the irradiation of the radiation X may be stopped.

On the other hand, if it is determined that operation is proper, the control section 60 proceeds to step S122 and, similarly to step S112, shortens the remaining accumulation duration bar displayed at the display 54 in correspondence with the passing of the imaging duration.

Then, in step S124, the control section 60 makes a determination as to whether the total accumulation duration has ended. That is, the control section 60 makes a determination as to whether the division imaging has completely finished. If the division imaging has not yet finished, the control section 60 proceeds to step S126.

In step S126, similarly to step S114, the control section 60 makes a determination as to whether there is an irradiation instruction from the user. If no irradiation instruction has been received, the control section 60 returns to step S122, continues to shorten the remaining accumulation duration bar, and repeats steps S122 to S126. On the other hand, if the control section 60 has received the irradiation instruction, the control section 60 returns to step S116 and performs division imaging for the next stage of the division imaging. Thereafter, steps S116 to S126 are repeated to perform the division imaging. In the case illustrated in FIG. 9, for the third stage of division imaging, a division region C is set at the position corresponding with the region of the window 35 of the shielding plate 34, and the radiation X passing through the imaging subject 18 is irradiated onto division region C to perform the division imaging. Hence, the fourth stage of division imaging is performed using a division region D, and the fifth stage of division imaging is performed using a division region E.

Alternatively, if it is determined in step S124 that the total accumulation duration has ended, the control section 60 proceeds to step S128. In step S128, the control section 60 turns on all of the TFT switches 74 in the radiation detector 26 of the electronic cassette 12, ending the accumulation of charges, commands the control section 106 of the electronic cassette 12 to read out the accumulated charges, and then ends the present processing. In response to this command, the control section 106 outputs control signals through the scan signal control circuits 104 to the gate lines 101 to turn the TFT switches 74 on. In response to the control signals, the accumulated charges collected at the lower electrodes 81 flow out into the signal lines from the pixels for radiographic image capture 100A.

The control section 106 of the electronic cassette 12 generates a radiographic image on the basis of the charges that are read out. As illustrated in FIG. 9, the generated radiographic image contains all of the radiographic images for the division regions A to E in a single radiographic image. The generated radiographic image is outputted to the console 20 and console 24 or the like.

If, in step S106, step S114 or step S126 described above, there is an irradiation instruction from the user after the irradiation timing has passed, the control section 60 may report to the user that the irradiation timing is late, or the like. When an irradiation timing is late, there is a risk that the accumulation duration will be shortened for the next and subsequent stages of division imaging, or that the division imaging will be finished incompletely. Therefore, it is preferable if a period that is a permissible range for mistiming of irradiation timings is established in advance, by experimentation or the like, and the control section 60 gives the report mentioned above to the user if there is an irradiation instruction outside the permissible range.

Second Exemplary Embodiment

In the first exemplary embodiment, the user instructs the irradiations of the radiation X. In the present exemplary embodiment, a case in which the radiographic imaging system 10 irradiates the radiation X automatically is described. As a method for automatically irradiating the radiation X, the console 20 may, for example, command the radiation irradiation device 16 to start an irradiation in accordance with the start of imaging at the respective division region after the movement by the electronic cassette movement section 32 and the like.

The structures of the radiographic imaging system 10, the electronic cassette 12, the console 20 and the console 24 are the same as in the first exemplary embodiment, so are not described here. The present exemplary embodiment differs from the first exemplary embodiment in that the console 24 compares the electronic signals detected from the pixels for radiation sensing 100B with a threshold and determines that the start of an irradiation of the radiation X is detected when the electronic signals are at least at the threshold. The present exemplary embodiment operates similarly to the first exemplary embodiment, apart from updating of the display at timings at which irradiations of radiation are detected.

FIG. 12 shows a flowchart depicting an example of the flow of the division imaging processing according to the present exemplary embodiment.

The division imaging processing according to the present exemplary embodiment is provided with step S107 instead of step S106 of the division imaging processing according to the first exemplary embodiment (see FIG. 8), step S115 instead of step S114, and step S127 instead of step S126. Other steps are the same as in the first exemplary embodiment, with the same step numbers, so are not described in detail here.

In steps S100 to S102, the same as in the first exemplary embodiment, the control section 60 makes a determination as to whether division imaging is possible. In the present exemplary embodiment, if it is determined in step S102 that division imaging is possible, the control section 60 proceeds to step S107.

In step S107, the control section 60 compares the electronic signals detected from the pixels for radiation sensing 100B provided in the region corresponding to division region A with the threshold for detecting the start of an irradiation, and if the electronic signals are at least at the threshold, determines that the start of an irradiation of the radiation X is detected. Because the electronic signals detected from the pixels for radiation sensing 100B are affected by the dark current, the threshold for detecting the start of an irradiation is preferably set in accordance with the dark current, similarly to the determination of whether or not operation is proper in the first exemplary embodiment.

The standby state continues until it is determined that an irradiation has started, and when it is determined that an irradiation has started, the control section 60 proceeds to step S108 and the first stage of division imaging is begun.

In step S108 to step S112, the same as in the first exemplary embodiment, the control section 60 starts the display of the state of progress of the imaging, and shortens the remaining accumulation duration bar as the imaging duration (accumulation duration) passes.

After step S112, the control section 60 proceeds to step S115 and, similarly to step S107, the control section 60 determines that the start of an irradiation of the radiation X is detected when the electronic signals detected from the pixels for radiation sensing 100B provided in a region corresponding to the division region for which division imaging is to be performed are at least at the threshold for detection.

When it is determined that an irradiation has started in step S115, the control section 60 proceeds to step S116, and the second or subsequent stage of division imaging is carried out. In step S116 to step S124, the same as in the first exemplary embodiment, the control section 60 updates the display of the state of progress of the imaging, makes a determination as to whether operation is proper, and shortens the remaining accumulation duration bar as the imaging duration (accumulation duration) passes.

In step S118, in addition to the determination as to whether operation is proper, a determination may be made as to whether the start of an irradiation of the radiation X has been misdetected. For example, as a result of the effects of an impact being applied to the electronic cassette 12 due to a movement of the imaging subject 18, or of external interference or the like, charges may be generated as noise in the radiation detector 26 and electronic signals may flow into the signal lines 73. There may be cases in which these flowing electronic signals are at or above the threshold for detection and the start of an irradiation of the radiation X is misdetected. Therefore, it is preferable to make a determination as to whether or not there has been a misdetection on the basis of the electronic signals detected from the pixels for radiation sensing 100B. A method for making the determination as to whether there is a misdetection is not particularly limited. For example, in the cases described above, the electronic signals flow only momentarily, or exhibit changes over time that are characteristic of noise. Therefore, the determination as to whether there is a misdetection may be made on the basis of changes over time of the electronic signals. In a case in which it is determined that there has been a misdetection, the control section 60 may restore the display of the state of progress of the imaging that has been updated in step S116 to the display before the update, and the control section 60 may return to step S116.

In the present exemplary embodiment, the determination as to whether the total accumulation duration has ended is made in step S124, and if the total accumulation duration has ended, the control section 60 proceeds to step S127. In step S127, the same as in step S115, the control section 60 determines that the start of an irradiation of the radiation X is detected if the electronic signals detected from the pixels for radiation sensing 100B are at least at the threshold for detection. If it is determined in step S127 that an irradiation has started, the control section 60 returns to step S116, and the division imaging is repeatedly performed in the same manner as in the first exemplary embodiment.

The same as in the first exemplary embodiment, if it is determined in step S124 that the total accumulation duration has ended, the control section 60 proceeds to step S128. In step S128, the same as in the first exemplary embodiment, the control section 60 turns on all the TFT switches 74 in the radiation detector 26, ending the accumulation of charges, commands the control section 106 of the electronic cassette 12 to read out the accumulated charges, and then ends the present processing.

As described hereabove, in the radiographic imaging system 10 according to the above exemplary embodiments, in a case of division imaging, the control section 60 of the console 24 displays the state of progress of the imaging at the display 50 of the UI section 25. If there is an instruction to start an irradiation of radiation from a user, or if the start of an irradiation of the radiation X is detected on the basis of electronic signals detected from the pixels for radiation sensing 100B, the control section 60 starts or updates the display of the state of progress of the imaging. The display of the state of progress of the imaging includes information relating to remaining imaging, which is, for example, a remaining accumulation duration bar representing the remaining accumulation duration, digits representing numbers of remaining irradiations, and marks representing irradiation timings. The remaining accumulation duration bar shows the remainder of the charge accumulation duration for the whole of the radiation detector 26. The control section 60 shortens the remaining accumulation duration bar with the passage of the imaging duration (the charge accumulation duration). The digits representing the numbers of remaining irradiations each indicate a number of remaining times the radiation X is to be irradiated at the electronic cassette 12 (the radiation detector 26). Each time the user instructs an irradiation, the number is counted down. The marks representing the irradiation timings prompt the user to instruct irradiations of the radiation X.

Therefore, the user can more easily perceive states of accumulation of charges at the radiation detector 26 and identify a remaining charge accumulation duration. Thus, in the radiographic imaging system 10, imaging of each division region into which the imaging region of the radiation detector is plurally divided may be carried out appropriately.

In the radiographic imaging system 10 according to the above exemplary embodiments, an electronic cassette for video imaging may be rendered unnecessary by division imaging; an image that looks like a video image, which may be called a pseudo-video image, may be displayed. Further, in division imaging by the radiographic imaging system 10, an imaging duration may be shortened compared to a case of video imaging. In a case of video imaging, successive still images are captured using the whole of the imaging region, and the still images are made into a video image by being successively displayed. Each time a still image is captured, the electronic cassette performs preparation operations, reading of the charges accumulated in the pixels, a reset and the like. Consequently, an imaging interval between the still images in video imaging is long. In contrast, in division imaging, because reading of charges and the like are not performed during the interval of division imaging and another division imaging, the imaging interval may be shortened. Thus, the imaging duration may be shortened compared to a case of video imaging.

In the above exemplary embodiments, the control section 60 of the console 24 at the electronic cassette 12 side includes the functions of the imaging control section and the display control section. However, the control section 40 of the console 20 may include both these functions, or the two functions may be provided at separate functional sections. Further, a case is described in which the processing described for the division imaging processing (see FIG. 8 and FIG. 12) is executed by the same functional section (the control section 60). However, the processing may be performed by alternative functional sections, depending on the processing. For example, the processing of steps S100 to S104 may be performed by the control section 40 of the console 20.

In the above exemplary embodiments, a case is described in which the electronic cassette 12 is moved in accordance with the imaging of the division regions, but this is not limiting. For example, because it is sufficient that the shielding plate 34 and the electronic cassette 12 be relatively moved, the shielding plate 34 may be moved. In a case in which the shielding plate 34 is moved, the radiation irradiation device 16 may also be moved in correspondence with movements of the shielding plate 34. It is also possible to not provide the shielding plate 34 but adjust an irradiation field that is irradiated by the radiation X from the radiation irradiation device 16 so as to move the imaging region of the radiation detector 26 on which the radiation X is irradiated (the imaging surface of the imaging table 14).

How the division regions are arranged is not limited by the above exemplary embodiments. For example, there may be four division regions, two in one direction along the imaging subject 18 by two in a direction orthogonal to the one direction.

In the above exemplary embodiments, the threshold of the standard for determining whether operation is proper and the threshold for detecting the start of an irradiation of radiation are changed in accordance with increases in the dark current as the accumulation duration passes. However, alternative changes and the like are possible. For example, the detected electronic signals may be corrected to take account of increases in the dark current.

The duration in which the remaining accumulation duration bar shortens may be altered in accordance with settings of the accumulation duration, the number of division regions remaining, the accumulation duration and the like.

In the above exemplary embodiments, the determination of whether operation is proper and the detection of the start of an irradiation of radiation are based on electronic signals detected from the pixels for radiation sensing 100B. However, alternative sensors may be provided instead of the pixels for radiation sensing 100B. For example, sensors for sensing the radiation X may be provided between the pixels 100. Furthermore, the structure of each pixel of the pixels for radiation sensing 100B is not limited to the structure described in the above exemplary embodiments.

In the above exemplary embodiments, a case is described in which the present disclosure is applied to the radiation detector 26 of an indirect conversion type that converts light converted from the radiation X to charges, but this is not limiting. For example, the present disclosure may be applied to a radiation detector of a direct conversion type that employs a material that converts radiation X directly to charges, such as amorphous selenium or the like, as the photoelectric conversion layer that absorbs the radiation X and converts the radiation X to charges.

In the above exemplary embodiments, an example of division imaging is described, but multiple exposure imaging is similar. Multiple exposure imaging is an imaging method in which the radiation X is irradiated at the same imaging region of the electronic cassette 12 plural times, between which charge accumulation states are maintained. Thus, multiple exposures are performed and sufficient radiation amounts that are required when the imaging subject 18 is a patient whose body is bulky (with thickness in the direction in which the radiation X passes) may be obtained. In particular, radiation irradiation devices that have been in use for a long time may have originally been fabricated to have a low irradiation output power. In a case in which this kind of radiation irradiation device is used for a bulky patient with a bulky body, multiple exposure imaging may be useful if a sufficient radiation amount may not be obtained from a single irradiation. As an example, in the above exemplary embodiments, in division imaging the remaining duration of the charge accumulation duration is displayed to show whether or not imaging corresponding to a number of divisions has been completed. Similarly, in multiple exposure imaging, the remaining duration may be displayed to show whether or not a plural number of irradiations has been completed.

Similarly, the numbers of remaining stages of imaging of division regions in the above exemplary embodiments may be replaced with numbers of remaining stages of irradiation in multiple exposure imaging.

In essence, the only difference is whether different regions (division regions) are irradiated in plural stages or whether the same region (the imaging region) is irradiated plural times. Thus, the value of displaying information relating to the imaging remaining until the completion of imaging at a display section is the same in both cases. In other respects too, the exemplary embodiments described above may be applied to multiple exposure imaging instead of division imaging as appropriate.

In other respects, structures, operations and the like of the radiographic imaging system 10, the electronic cassette 12, the console 20, the console 24 and the like described in the present exemplary embodiments are examples and these may be modified in accordance with circumstances within a scope not departing from the spirit of the present disclosure.

The radiation of the present disclosure is not particularly limited by the present exemplary embodiments; X-rays, gamma rays and so forth may be employed.

Related technologies include a method of, in division imaging, reading charges all together after the completion of imaging of all division regions rather than reading the charges each time a division region is imaged. In a method of reading charges all together, there may be cases in which a limit is applied to a charge accumulation duration.

Related technologies further include, in multiple exposure imaging, a method of reading charges all together after a predetermined number of irradiations rather than reading charges once for each irradiation between the multiple exposures. In this case, similarly, there may be cases in which a limit is applied to the charge accumulation duration.

The present disclosure provides a radiographic imaging system that may appropriately perform imaging of respective division regions into which an imaging region of a radiation detector is plurally divided or imaging that performs multiple exposures of the same imaging region, a method of controlling the radiographic imaging system, and a recording medium storing a program for controlling the radiographic imaging system.

The radiographic imaging system includes: a radiation detector including an imaging region in which a plurality of pixels are provided, each pixel including a sensor portion that generates charges in accordance with radiation amounts of irradiated radiation and accumulates the generated charges during an accumulation period, and a switching element that reads out the charges from the sensor portion after the accumulation period; an imaging control section that images a radiographic image by one of sequentially imaging radiographic images during the accumulation period using division regions, into which the imaging region of the radiation detector is plurally divided, one at a time, or performing a multiple exposure in which the same region of the imaging region of the radiation detector is irradiated a plurality of times during the accumulation period; and a display control section that displays, at a display section, information relating to remaining imaging until the imaging is complete, the information being for representing a state of progress of the imaging by the imaging control section.

In the radiographic imaging system, the information relating to remaining imaging until the imaging is complete includes a remaining duration of the imaging by the imaging control section.

In the radiographic imaging system, the remaining duration of the imaging includes a remaining duration of the accumulation period during the imaging.

In the radiographic imaging system, the information relating to remaining imaging until the imaging is complete includes a number of cycles of imaging at the division regions by the imaging control section.

The radiographic imaging system is provided with a sensing portion that senses irradiated radiation at the imaging region of the radiation detector.

In the radiographic imaging system, the sensing portion senses the radiation in each division region, and the radiographic imaging system includes a detection section that detects the start of an irradiation of radiation on the basis of sensing results from the sensing portion.

In the radiographic imaging system, the display control section updates the display of the state of progress of the imaging when the detection section detects the start of an irradiation. In the radiographic imaging system, the display control section updates the display of the state of progress of the imaging when an instruction to start an irradiation of radiation is detected.

In the radiographic imaging system, the accumulation period of the radiation detector is set in advance in accordance with a dark current that occurs in the imaging region.

The radiographic imaging system is provided with a radiation irradiation device that irradiates radiation at the radiation detector.

The method of controlling the radiographic imaging system is a method of controlling a radiographic imaging system that employs a radiation detector that includes an imaging region in which a plurality of pixels are provided, each pixel including a sensor portion that generates charges in accordance with radiation amounts of irradiated radiation and accumulates the generated charges during an accumulation period, and a switching element that reads out the charges from the sensor portion after the accumulation period, the method including: imaging a radiographic image by, with an imaging control section, one of sequentially imaging radiographic images during the accumulation period using division regions, into which the imaging region of the radiation detector is plurally divided, one at a time, or performing a multiple exposure in which the same region of the imaging region of the radiation detector is irradiated a plurality of times during the accumulation period; and with a display control section, displaying, at a display section, information relating to remaining imaging until the imaging is complete, the information being for representing a state of progress of the imaging by the imaging control section.

A non-transitory recording medium stores a program that causes a computer to execute a process controlling a radiographic imaging system, the radiographic imaging system including a radiation detector that includes an imaging region in which a plurality of pixels are provided, each pixel including a sensor portion that generates charges in accordance with radiation amounts of irradiated radiation and accumulates the generated charges during an accumulation period, and a switching element that reads out the charges from the sensor portion after the accumulation period, and the process including: imaging a radiographic image by, with an imaging control section, one of sequentially imaging radiographic images during the accumulation period using division regions, into which the imaging region of the radiation detector is plurally divided, one at a time, or performing a multiple exposure in which the same region of the imaging region of the radiation detector is irradiated a plurality of times during the accumulation period; and with a display control section, displaying, at a display section, information relating to remaining imaging until the imaging is complete, the information representing a state of progress of the imaging by the imaging control section.

According to the present disclosure, imaging of respective division regions into which an imaging region of a radiation detector is plurally divided or imaging that applies multiple exposures to the same imaging region may be carried out appropriately.

What is claimed is:

1. A radiographic imaging system comprising:
    a radiation detector including an imaging region in which a plurality of pixels are provided, each pixel including:
        a sensor portion that generates charges in accordance with radiation amounts of irradiated radiation and accumulates the generated charges during an accumulation period, and
        a switching element that reads out the charges from the sensor portion after the accumulation period;
    an imaging control section that images a radiographic image by
    sequentially imaging radiographic images during the accumulation period using division regions, into which the imaging region of the radiation detector is plurally divided, one at a time; and
    a display control section that displays, at a display section, information relating to remaining imaging until the imaging is complete, the information including a remaining duration of the accumulation period during the imaging by the imaging control section, and the information representing a state of progress of the imaging by the imaging control section, wherein:
    after imaging of all division regions has been completed, charges are read out from all of the pixels together, and
    the accumulation period of the radiation detector is set in advance in accordance with a dark current that occurs in the imaging region.

2. The radiographic imaging system of claim 1, wherein the information relating to remaining imaging until the imaging is complete includes a remaining number of cycles of imaging at the division regions by the imaging control section.

3. The radiographic imaging system of claim 1, further comprising a sensing portion that is between the pixels and that senses irradiated radiation at the imaging region of the radiation detector.

4. The radiographic imaging system of claim 3, wherein the sensing portion senses the radiation in each division region, and the radiographic imaging system further includes a detection section that detects the start of an irradiation of radiation on the basis of sensing results from the sensing portion.

5. The radiographic imaging system of claim 4, wherein the display control section updates the display of the state of progress of the imaging in a case that the detection section detects the start of an irradiation.

6. The radiographic imaging system of claim 1, wherein the display control section updates the display of the state of progress of the imaging in a case that an instruction to start an irradiation of radiation is detected.

7. The radiographic imaging system of claim 1, wherein the radiation detector further includes a radiation irradiation device that irradiates radiation.

8. A method of controlling a radiographic imaging system, wherein:
    the radiographic imaging system includes:
        a radiation detector that includes an imaging region in which a plurality of pixels are provided, each pixel including
        a sensor portion that generates charges in accordance with radiation amounts of irradiated radiation and accumulates the generated charges during an accumulation period, and
        a switching element that reads out the charges from the sensor portion after the accumulation period,
    and the method comprises:
    imaging a radiographic image by, with an imaging control section,
    sequentially imaging radiographic images during the accumulation period using division regions, into which the imaging region of the radiation detector is plurally divided, one at a time;
    with a display control section, displaying, at a display section, information relating to remaining imaging until the imaging is complete, the information including a remaining duration of the accumulation period during the imaging by the imaging control section, and the information representing a state of progress of the imaging by the imaging control section; and after imaging of all division regions has been completed, reading charges out from all of the pixels together, wherein the accumulation period of the radiation detector is set in advance in accordance with a dark current that occurs in the imaging region.

9. A non-transitory recording medium storing a program that causes a computer to execute a process for controlling a radiographic imaging system, wherein:

the radiographic imaging system includes:

a radiation detector that includes an imaging region in which a plurality of pixels are provided, each pixel including a sensor portion that generates charges in accordance with radiation amounts of irradiated radiation and accumulates the generated charges during an accumulation period, and a switching element that reads out the charges from the sensor portion after the accumulation period, and the process comprises:

imaging a radiographic image by, with an imaging control section, sequentially imaging radiographic images during the accumulation period using division regions, into which the imaging region of the radiation detector is plurally divided, one at a time;

with a display control section, displaying, at a display section, information relating to remaining imaging until the imaging is complete, the information including a remaining duration of the accumulation period during the imaging by the imaging control section, and the information representing a state of progress of the imaging by the imaging control section; and after imaging of all division regions has been completed, reading charges out from all of the pixels together, wherein the accumulation period of the radiation detector is set in advance in accordance with a dark current that occurs in the imaging region.

* * * * *